US007514261B2

(12) United States Patent
Edelberg et al.

(10) Patent No.: US 7,514,261 B2
(45) Date of Patent: Apr. 7, 2009

(54) PLATELET-DERIVED GROWTH FACTOR PROTECTION OF CARDIAC MYOCARDIUM

(75) Inventors: Jay M. Edelberg, New York, NY (US); Shahin Rafii, Great Neck, NY (US); Mun K. Hong, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 515 days.

(21) Appl. No.: 10/215,271

(22) Filed: Aug. 8, 2002

(65) Prior Publication Data
US 2003/0091547 A1 May 15, 2003

Related U.S. Application Data

(60) Provisional application No. 60/357,328, filed on Feb. 15, 2002, provisional application No. 60/311,238, filed on Aug. 9, 2001.

(51) Int. Cl.
*C12N 5/00* (2006.01)
*C12N 5/08* (2006.01)

(52) U.S. Cl. .................. 435/405; 435/366; 435/372; 435/392

(58) Field of Classification Search ............ 435/325, 435/93.21, 366, 372, 392, 405; 424/93.27
See application file for complete search history.

(56) References Cited

U.S. PATENT DOCUMENTS

| | | | | |
|---|---|---|---|---|
| 5,955,436 | A | 9/1999 | Kunkle, Jr. | 514/21 |
| 5,962,313 | A | 10/1999 | Podsakoff et al. | |
| 5,980,887 | A | 11/1999 | Isner et al. | |
| 6,077,987 | A | 6/2000 | Breitbart et al. | 623/11 |
| 6,086,866 | A | 7/2000 | Kouri | 424/85.1 |
| 6,235,713 | B1 | 5/2001 | Achen et al. | 514/12 |
| 6,328,958 | B1 | 12/2001 | Amalfitano et al. | |
| 6,350,731 | B1 | 2/2002 | Jehanli et al. | 514/12 |
| 6,398,816 | B1 | 6/2002 | Breitbart et al. | 623/23.72 |
| 6,676,679 | B1* | 1/2004 | Mueller et al. | 606/185 |
| 6,818,439 | B1* | 11/2004 | Jolly et al. | 435/320.1 |
| 7,135,171 | B2 | 11/2006 | Edelberg | |
| 2002/0197232 | A1* | 12/2002 | Snodgrass et al. | 424/85.1 |

OTHER PUBLICATIONS

Hiragun et al. (1998, J. Invest. Dermatol., 111:213-217).*
D'Ippolito et al. (1999, Journal of Bone and Mineral Research, 14; 1115-1122).*
Webb et al., (1998, Clin Sci (Lond), 94: 395-404, abstract).*
Caplice et al. (1997, JACC, 29: 1536-1541).*
Schmitz, et al., 1995, Leukemia Research, 19: 629-637.*
Folkman and Shing, 1992, The Journal of Biological Chemistry, 267: 10931-10934.*
Gehling et al., 2000, Blood, 95: 3106-3112.*
Axel et al., 1997, Circulation, 96: 636-645.*

Ataliotis, P.,et al. ,"Distribution and Function of Platelet-Derived Growth Factor and Their Receptors during Embryogenesis", *International Review of Cytology*, 172, (1997),pp. 95-127.
Betsholtz, C.,"Role of platelet-derived growth factors in mouse development", *Int. J. Dev. Biol.*, 39, (1995),pp. 817-825.
Christini, D.,et al. ,"Direct biologically based biosensing of dynamic physiological function", *Am. J. Physiol. Heart Circ. Physiol.*, 280, (2001),pp. H2006-H2010.
Davis, T.,et al. ,"Ex Vivo Expansion of Primitive Murine Hematopoietic Progenitor Cells on Procine Endothelial Cells", *Transplatation Proceedings*, 29, (1997),p. 2005.
Deuel,T.,et al. ,"Human Platelet-derived Growth Factor",*The Journal of Biological Chemistry*, 256(17), (1981),pp. 8896-8899.
Edelberg, J.,et al. ,"Enhanced myocyte-based biosensing of the blood-borne signals regulating chronotropy", *The Journal of Applied Physiology*, 92, (2002),pp. 581-585.
Edelberg, J.,et al. ,"PDGF Mediates Cardiac Microvascular Communication", *Journal of Clinical Investigation*, 102(4), (1998),pp. 837-843.
Edelberg, J.,et al. ,"Young Adult Bone Marrow-Derived Endothelilial Precursor Cells Restore Aging-Impaired Cardiac Angiogenic Function", *Circulation Research*, 90, (2002),pp. e89-e93.
Edleberg, J.,et al. ,"Platelet-Derived Growth Facto-AB Limits the Extent of Myocardial Infarction in a Rat Model", *Circulation*, 105, (2002),pp. 608-613.
Hakuno, D.,et al. ,"Bone Marrow-Derived Regenerated Cardiomyocytes (CMG Cells) Express Functional Adrenergic and Muscarinic Receptors", *Circulation*, 105, http://www.circulationaha.org,(2002),pp. 380-386.
Heldin , C.,et al. ,"Chemical and Biological Properties of a Growth Factor From Human -Cultured Osteosarcoma Cells: Resemblance with Platelet-Derived Growth Factor", *Journal of Cellular Physiology*, 105, (1980),pp. 235-246.
Jackson, K.,et al. ,"Regeneration of ischemic cardiac muscle and vascular endothelium by adult stem cells", *The Journal of Clinical Investigation*, 107(11), (2001),pp. 1395-1402.
Makino, S.,et al. ,"Cardiomyocytes can be generated from marrow stromal cells in vitro", *The Journal of Clinical Investigation*, 103(5), (1999),pp. 697-705.
Malouf, N.,et al. ,"Adult-Derived Stem Cells from the Liver Become Myocytes in the Heart in Vivo", *American Journal of Pathology*, 158(6), (2001),pp. 1929-1935.
Mohle, R.,et al. ,"Expression of interleukin-5 by human bome marrow microvascular endothelial cells: implications for the regulation of eosinophilopoieses in vivo", *British Journal of Haematology*, 99, (1997),pp. 732-738.
Orlic, D.,et al. ,"Bone marrow cells regenerate infarcted myocardium", *Nature*, 410, (2001),pp. 701-705.
Palmer, T.,et al. ,"Vascular Niche for Adult Hippocampal Neurogenesis", *The Journal of Comparative Neurology*, 425, (2000),pp. 479-494.
Rafii, S.,et al. ,"Human Bone Marrow Microvascular Endothelial Cells Support Long-Term Proliferation and Differentiation of Myeloid and Megakaryocytic Progenitors", *Blood*, 86(9), (1995),pp. 3353-3363.

(Continued)

*Primary Examiner*—Joanne Hama
(74) *Attorney, Agent, or Firm*—Schwegman, Lundberg & Woessner, P.A.

(57) ABSTRACT

The invention provides methods of treating and preventing loss of tissue vascularization that can occur, for example, upon aging.

6 Claims, 11 Drawing Sheets

OTHER PUBLICATIONS

Rafii, S., et al., "Regulation of Hematopoiesis by Microvascular Endothelium", *Leuk. Lymphoma*, 27, (1997), pp. 375-386.

Raines, E., et al., "Platelet-derived Growth Factor", *The Journal of Biological Chemistry*, 257(9), (1982), pp. 5154-5160.

Wang, T., et al., "Differential expression of nitric oxide synthases in EGF-responsive mouse neural precursor cells", *Cell Tissue*, 296, (1999), pp. 489-497.

Weinsaft, J., et al., "Aging-Associated Changes in Vascular Activity: A Potential Link To Geriatic Cardiovascular Disease", *The American Journal of Geriatric Cardiology*, 10(6), (2001), pp. 348-354.

Yourey, P, et al., "Vascular Endothial Cell Growth Factors Promote the In Vitro Development of Rat Photoreceptor Cells", *The Journal of Neuroscience*, 20(18), (2000), pp. 6781-6788.

Brown, B. D., et al., "Dangerous Liaisons: the Role of "Danger" Signals in the Immune Response to Gene Therapy", *Blood 100*(4), (2002), 1133-1140.

Chiu, R. C., "Adult Stem Cell Therapy for Heart Failure", *Expert Opinion on Biological Therapy*, 3(2), (2003), 215-225.

Edelberg, J. M., et al., "Restoration of Senesecent Cardiac Angiogenic Activity", *Circulation*, 104 (17) *Supplement*, (Abstract 746), (Oct. 23, 2001), p. 11.0.

Itescu, S., et al., "New Directions in Straegies Using Cell Therapy for Heart Disease", *Journal of Molecular Medicine*, 81, (2003), 288-296.

Juengst, E. T., "What Next for Human Gene Therapy?", *BMJ*, 326, (2003), 1410-1411.

Rafii, S., et al., "Therapeutic Stem and Progenitor Cell Transplantation for Organ Vascularization and Regeneration", *Nature Medicine*, 9(6), (2003), 702-712.

Rosenberg, L. E., et al., "Gene Therapist, Heal Thyself", *Science*, 287, (2000), 1751.

Touchette, N., "Gene Therapy: Not Ready for Prime Time", *Nature Medicine*, 2(1), (1996), 7-8.

Xaymardan, M., et al., "Platelet-Derived Growth Factor-AB Promotes the Generation of Adult Bone Marrow-Derived Cardiac Myocytes", *Circulation Research*, 94, (2004), e39-e45.

U.S. Appl. No. 10/367,639, Advisory Action mailed Mar. 28, 2005, 3 pgs.

U.S. Appl. No. 10/367,639, Final Office Action Jan. 4, 2006, 10 pgs.

U.S. Appl. No. 10/367,639, Final Office Action mailed Dec. 3, 2004, 13 pgs.

U.S. Appl. No. 10/367,639, Non Final Office Action mailed May 21, 2004, 17 pgs.

U.S. Appl. No. 10/367,639, Non Final Office Action mailed Jun. 28, 2005, 13 pgs.

U.S. Appl. No. 10/367,639, Notice of Allowance mailed Jun. 16, 2004, 9 pgs.

U.S. Appl. No. 10/367,639, Response filed Mar. 3, 2005 to Final Office Action mailed Dec. 3, 2004, 10 pgs.

U.S. Appl. No. 10/367,639, Response filed Mar. 28, 2006 to Final Office Action Jan. 4, 2006, 4 pgs.

U.S. Appl. No. 10/367,639, Response filed Sep. 21, 2004 to Non Final Office Action mailed May 21, 2004, 15 pgs.

U.S. Appl. No. 10/367,639, Response filed Sep. 28, 2005 to Non Final Office Action mailed Jun. 28, 2005, 8 pgs.

\* cited by examiner

Control　　　PDGF

SEQUENCE LISTING

<160> NUMBER OF SEQ ID NOS: 34

<210> SEQ ID NO 1
<211> LENGTH: 204
<212> TYPE: PRT
<213> ORGANISM: Homo sapiens

<400> SEQUENCE: 1

```
Met Arg Thr Trp Ala Cys Leu Leu Leu Gly Cys Gly Tyr Leu Ala
1               5                   10                  15

His Ala Leu Ala Glu Glu Ala Glu Ile Pro Arg Glu Leu Ile Glu Arg
            20                  25                  30

Leu Ala Arg Ser Gln Ile His Ser Ile Arg Asp Leu Gln Arg Leu Leu
            35                  40                  45

Glu Ile Asp Ser Val Gly Ala Glu Asp Ala Leu Glu Thr Asn Leu Arg
     50                  55                  60

Ala His Gly Ser His Thr Val Lys His Val Pro Glu Lys Arg Pro Val
65                  70                  75                  80

Pro Ile Arg Arg Lys Arg Ser Ile Glu Glu Ala Ile Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Ser Asn Leu Asn Pro Asp His Arg Glu Glu Glu
            180                 185                 190

Thr Gly Arg Arg Arg Glu Ser Gly Lys Lys Arg Lys
        195                 200
```

<210> SEQ ID NO 2
<211> LENGTH: 196
<212> TYPE: PRT

<213> ORGANISM: Mus musculus

<400> SEQUENCE: 2

Met Arg Thr Trp Ala Cys Leu Leu Leu Gly Cys Gly Tyr Leu Ala
1               5                   10                  15

His Ala Leu Ala Glu Glu Ala Glu Ile Pro Arg Glu Leu Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ala Glu Asp Ala Leu Glu Thr Ser Leu Arg
50                  55                  60

Ala His Gly Ser His Ala Ile Asn His Val Pro Glu Lys Arg Pro Val
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu Asp Leu Glu
                165                 170                 175

Cys Ala Cys Ala Thr Ser Asn Leu Asn Pro Asp His Arg Glu Glu Glu
            180                 185                 190

Thr Asp Val Arg
        195

<210> SEQ ID NO 3
<211> LENGTH: 241
<212> TYPE: PRT
<213> ORGANISM: Homo sapiens

<400> SEQUENCE: 3

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
130                 135                 140

Gln Val Gln Leu Arg Pro Val Gln Val Arg Lys Ile Glu Ile Val Arg

```
                145                 150                 155                 160
Lys Lys Pro Ile Phe Lys Lys Ala Thr Val Thr Leu Glu Asp His Leu
            165                 170                 175
Ala Cys Lys Cys Glu Thr Val Ala Ala Ala Arg Pro Val Thr Arg Ser
            180                 185                 190
Pro Gly Gly Ser Gln Glu Gln Arg Ala Lys Thr Pro Gln Thr Arg Val
            195                 200                 205
Thr Ile Arg Thr Val Arg Val Arg Arg Pro Lys Gly Lys His Arg
    210                 215                 220
Lys Phe Lys His Thr His Asp Lys Thr Ala Leu Lys Glu Thr Leu Gly
225                 230                 235                 240
Ala

<210> SEQ ID NO 4
<211> LENGTH: 241
<212> TYPE: PRT
<213> ORGANISM: Mus musculus

<400> SEQUENCE: 4

Met Asn Arg Cys Trp Ala Leu Phe Leu Pro Leu Cys Cys Tyr Leu Arg
1               5                   10                  15
Leu Val Ser Ala Glu Gly Asp Pro Ile Pro Glu Glu Leu Tyr Glu Met
            20                  25                  30
Leu Ser Asp His Ser Ile Arg Ser Phe Asp Asp Leu Gln Arg Leu Leu
        35                  40                  45
His Arg Asp Ser Val Asp Glu Asp Gly Ala Glu Leu Asp Leu Asn Met
    50                  55                  60
Thr Arg Ala His Ser Gly Val Glu Leu Glu Ser Ser Ser Arg Gly Arg
65                  70                  75                  80
Arg Ser Leu Gly Ser Leu Ala Ala Ala Glu Pro Ala Val Ile Ala Glu
                85                  90                  95
Cys Lys Thr Arg Thr Glu Val Phe Gln Ile Ser Arg Asn Leu Ile Asp
            100                 105                 110
Arg Thr Asn Ala Asn Phe Leu Val Trp Pro Pro Cys Val Glu Val Gln
        115                 120                 125
Arg Cys Ser Gly Cys Cys Asn Asn Arg Asn Val Gln Cys Arg Ala Ser
    130                 135                 140
Gln Val Gln Met Arg Pro Val Gln Val Arg Lys Ile Glu Ile Val Arg
145                 150                 155                 160
Lys Lys Pro Ile Phe Lys Lys Ala Thr Val Thr Leu Glu Asp His Leu
            165                 170                 175
Ala Cys Lys Cys Glu Thr Ile Val Thr Pro Arg Pro Val Thr Arg Ser
            180                 185                 190
Pro Gly Thr Ser Arg Glu Gln Arg Ala Lys Thr Pro Gln Ala Arg Val
            195                 200                 205
Thr Ile Arg Thr Val Arg Ile Arg Arg Pro Lys Gly Lys His Arg
    210                 215                 220
Lys Phe Lys His Thr His Asp Lys Ala Ala Leu Lys Glu Thr Leu Gly
225                 230                 235                 240
Ala

<210> SEQ ID NO 5
<211> LENGTH: 161
<212> TYPE: PRT
<213> ORGANISM: Homo sapiens
```

<400> SEQUENCE: 5

```
Arg Ser Leu Gly Ser Leu Thr Ile Ala Glu Pro Ala Met Ile Ala Glu
 1               5                  10                  15
Cys Lys Thr Arg Thr Glu Val Phe Glu Ile Ser Arg Arg Leu Ile Asp
            20                  25                  30
Arg Thr Asn Ala Asn Phe Leu Val Trp Pro Pro Cys Val Glu Val Gln
        35                  40                  45
Arg Cys Ser Gly Cys Cys Asn Asn Arg Asn Val Gln Cys Arg Pro Thr
    50                  55                  60
Gln Val Gln Leu Arg Pro Val Gln Val Arg Lys Ile Glu Ile Val Arg
65                  70                  75                  80
Lys Lys Pro Ile Phe Lys Lys Ala Thr Val Thr Leu Glu Asp His Leu
                85                  90                  95
Ala Cys Lys Cys Glu Thr Val Ala Ala Ala Arg Pro Val Thr Arg Ser
            100                 105                 110
Pro Gly Gly Ser Gln Glu Gln Arg Ala Lys Thr Pro Gln Thr Arg Val
        115                 120                 125
Thr Ile Arg Thr Val Arg Val Arg Pro Pro Lys Gly Lys His Arg
    130                 135                 140
Lys Phe Lys His Thr His Asp Lys Thr Ala Leu Lys Glu Thr Leu Gly
145                 150                 155                 160
Ala
```

<210> SEQ ID NO 6
<211> LENGTH: 119
<212> TYPE: PRT
<213> ORGANISM: Homo sapiens

<400> SEQUENCE: 6

```
Met Asn Arg Cys Trp Ala Leu Phe Leu Ser Leu Cys Cys Tyr Leu Arg
 1               5                  10                  15
Leu Val Ser Ala Glu Gly Asp Pro Ile Pro Glu Glu Leu Tyr Glu Met
            20                  25                  30
Leu Ser Asp His Ser Ile Arg Ser Phe Asp Asp Leu Gln Arg Leu Leu
        35                  40                  45
His Gly Asp Pro Gly Glu Glu Asp Gly Ala Glu Leu Asp Leu Asn Met
    50                  55                  60
Thr Arg Ser His Ser Gly Gly Glu Leu Glu Ser Leu Ala Arg Gly Arg
65                  70                  75                  80
Arg Ser Leu Gly Ser Leu Thr Ile Ala Glu Pro Ala Met Ile Ala Glu
                85                  90                  95
Cys Lys Thr Arg Thr Glu Val Phe Glu Ile Ser Arg Arg Leu Ile Asp
            100                 105                 110
Arg Thr Asn Ala Asn Phe Leu
        115
```

<210> SEQ ID NO 7
<211> LENGTH: 20
<212> TYPE: DNA
<213> ORGANISM: Mus musculus

<400> SEQUENCE: 7
tcaaggtggc caaagtggag     20

<210> SEQ ID NO 8

-continued

```
<211> LENGTH: 20
<212> TYPE: DNA
<213> ORGANISM: Mus musculus

<400> SEQUENCE: 8
ctctctgtga caaggaagct                                               20

<210> SEQ ID NO 9
<211> LENGTH: 20
<212> TYPE: DNA
<213> ORGANISM: Mus musculus

<400> SEQUENCE: 9
atcgccgagt gcaagacgcg                                               20

<210> SEQ ID NO 10
<211> LENGTH: 20
<212> TYPE: DNA
<213> ORGANISM: Mus musculus

<400> SEQUENCE: 10
aagcaccatt ggccgtccga                                               20

<210> SEQ ID NO 11
<211> LENGTH: 20
<212> TYPE: DNA
<213> ORGANISM: Mus musculus

<400> SEQUENCE: 11
acagagactg agcgctgaca                                               20

<210> SEQ ID NO 12
<211> LENGTH: 20
<212> TYPE: DNA
<213> ORGANISM: Mus musculus

<400> SEQUENCE: 12
ttccaagaag gaaggaagca                                               20

<210> SEQ ID NO 13
<211> LENGTH: 30
<212> TYPE: DNA
<213> ORGANISM: Mus musculus

<400> SEQUENCE: 13
ggatccatga actttctgct gctgtcttgg                                    30

<210> SEQ ID NO 14
<211> LENGTH: 27
<212> TYPE: DNA
<213> ORGANISM: Mus musculus

<400> SEQUENCE: 14
ttctggcttt gtcctgtctt tctttgg                                       27

<210> SEQ ID NO 15
<211> LENGTH: 20
<212> TYPE: DNA
<213> ORGANISM: Mus musculus

<400> SEQUENCE: 15
cagcttgctc cttcctcatc                                               20
```

```
<210> SEQ ID NO 16
<211> LENGTH: 20
<212> TYPE: DNA
<213> ORGANISM: Mus musculus

<400> SEQUENCE: 16
tctggagagc aaaccaacca                                                    20

<210> SEQ ID NO 17
<211> LENGTH: 20
<212> TYPE: DNA
<213> ORGANISM: Mus musculus

<400> SEQUENCE: 17
tgtccaaggt ctgaagaaga                                                    20

<210> SEQ ID NO 18
<211> LENGTH: 20
<212> TYPE: DNA
<213> ORGANISM: Mus musculus

<400> SEQUENCE: 18
caggacaaac accacatcca                                                    20

<210> SEQ ID NO 19
<211> LENGTH: 20
<212> TYPE: DNA
<213> ORGANISM: Mus musculus

<400> SEQUENCE: 19
caagcggtcg tgaatgacac                                                    20

<210> SEQ ID NO 20
<211> LENGTH: 21
<212> TYPE: DNA
<213> ORGANISM: Mus musculus

<400> SEQUENCE: 20
cactgccttg actgtcttaa g                                                  21

<210> SEQ ID NO 21
<211> LENGTH: 21
<212> TYPE: DNA
<213> ORGANISM: Mus musculus

<400> SEQUENCE: 21
gtgggccgct ctaggcacca a                                                  21

<210> SEQ ID NO 22
<211> LENGTH: 24
<212> TYPE: DNA
<213> ORGANISM: Mus musculus

<400> SEQUENCE: 22
ctctttgatg tcacgcacga tttc                                               24

<210> SEQ ID NO 23
<211> LENGTH: 21
<212> TYPE: DNA
<213> ORGANISM: Mus musculus

<400> SEQUENCE: 23
gtgggccgct ctaggcacca a                                                  21
```

```
<210> SEQ ID NO 24
<211> LENGTH: 24
<212> TYPE: DNA
<213> ORGANISM: Mus musculus

<400> SEQUENCE: 24
ctctttgatg tcacgcacga tttc                                          24

<210> SEQ ID NO 25
<211> LENGTH: 20
<212> TYPE: DNA
<213> ORGANISM: Mus musculus

<400> SEQUENCE: 25
tcaaggtggc caaagtggag                                               20

<210> SEQ ID NO 26
<211> LENGTH: 20
<212> TYPE: DNA
<213> ORGANISM: Mus musculus

<400> SEQUENCE: 26
ctctctgtga caaggaagct                                               20

<210> SEQ ID NO 27
<211> LENGTH: 20
<212> TYPE: DNA
<213> ORGANISM: Mus musculus

<400> SEQUENCE: 27
atcgccgagt gcaagacgcg                                               20

<210> SEQ ID NO 28
<211> LENGTH: 20
<212> TYPE: DNA
<213> ORGANISM: Mus musculus

<400> SEQUENCE: 28
aagcaccatt ggccgtccga                                               20

<210> SEQ ID NO 29
<211> LENGTH: 20
<212> TYPE: DNA
<213> ORGANISM: Mus musculus

<400> SEQUENCE: 29
tgtccaaggt ctgaagaaga                                               20

<210> SEQ ID NO 30
<211> LENGTH: 20
<212> TYPE: DNA
<213> ORGANISM: Mus musculus

<400> SEQUENCE: 30
caggacaaac accacatcca                                               20

<210> SEQ ID NO 31
<211> LENGTH: 20
<212> TYPE: DNA
<213> ORGANISM: Mus musculus

<400> SEQUENCE: 31
caagcggtcg tgaatgacac                                               20
```

```
<210> SEQ ID NO 32
<211> LENGTH: 21
<212> TYPE: DNA
<213> ORGANISM: Mus musculus

<400> SEQUENCE: 32
cactgccttg actgtcttaa g                                              21

<210> SEQ ID NO 33
<211> LENGTH: 23
<212> TYPE: DNA
<213> ORGANISM: Mus musculus

<400> SEQUENCE: 33
ggaagagtga gcggccatca agg                                            23

<210> SEQ ID NO 34
<211> LENGTH: 22
<212> TYPE: DNA
<213> ORGANISM: Mus musculus

<400> SEQUENCE: 34
ctgctggaga ggttattcct cg                                             22
```

PLATELET-DERIVED GROWTH FACTOR PROTECTION OF CARDIAC MYOCARDIUM

RELATED APPLICATIONS

This application claims the benefit of priority under 35 U.S.C. 119(e) to U.S. Provisional Patent Application Ser. Nos. 60/311,238, filed Aug. 9, 2001, and 60/357,328, filed Feb. 15, 2002, both of which are incorporated herein by reference.

The invention described in this application was made with funds from the National Heart Lung and Blood Institute, Grant Number P01 HL-59312. The United States government has certain rights in the invention.

BACKGROUND OF THE INVENTION

Ischemic heart disease is the most common cause of morbidity and mortality in the population over the age of sixty-five. Sullivan, L. W. 1990. Healthy people 2000. *N Engl J Med.* 323:1065-1067; Wei, J. Y. 1992. Age and the cardiovascular system. *N Engl J Med.* 327:1735-1739; Association, A. H. 1993-1995. Heart and stroke facts statistical supplement/1994-1996. Dallas, Tex.: The Association. Elucidation of the cellular and molecular pathways that are impaired with aging is critical to develop specific strategies to prevent and reduce the pathology of cardiovascular disease associated with advancing age.

In younger individuals, myocardial ischemia induces the development of a collateral vasculature supply that partially protects the cardiac tissue from subsequent coronary events. Hirai et al. (1989) *Circulation.* 79:791-796; Ejiri et al. (1990) *J Cardiol.* 20:31-37; Kodama et al. (1996). *J Am Coll Cardiol.* 27:1133-1139; Banerjee et al., (1993) *Int J Cardiol.* 38:263-271. However, angiogenesis is impaired in older heart and peripheral vascular beds. Hudlicka et al. (1996) *J Vasc Res.* 33:266-287; Isoyama (1994) *Drugs Aging.* 5:102-115; Tomanek et al. (1990) *Am J Physiol.* 259:H1681-1687; Anversa et al. (1994) *Am J Physiol.* 267:H1062-1073; Azhar et al. (1999) *Exp Gerontol.* 34:699-714; Rakusan et al. (1994) *Cardiovasc Res.* 28:969-972; Rivard et al. (1999) *Circulation.* 99:111-120; Reed et al. (2000) *J Cell Biochem.* 77:116-126. The etiology of the impaired angiogenic activity in the senescent heart is not known. In fact, despite recent advances in our understanding of the molecular pathways regulating angiogenesis during embryonic development, the mechanistic alterations in angiogenic function in the senescent vasculature are not well understood. Therefore, new approaches are needed for counteracting the age-associated changes in angiogenic pathways within the cardiac endothelium.

SUMMARY OF THE INVENTION

According to the invention, interventions targeted at reversing the lack of myocyte generation and the lack of cellular communication in senescent cardiac tissues may decrease the susceptibility to vascular disease in the aging heart. In particular, the invention provides methods for treating aging mammalian vascular and heart tissues. In one embodiment, endothelial precursor cells are administered. Such cells have the ability to find their way to and then integrate into vascular tissues, for example, cardiac tissues. After becoming associated with vascular tissues such as cardiac tissues, these endothelial precursor cells can restore angiogenesis and/or generate myocytes. Moreover, such endothelial precursor cells can deliver PDGF to cardiac tissues, wherein the PDGF is also useful for restoring angiogenesis in the peripheral vasculature and in senescent cardiac tissues.

The invention provides methods for treating or preventing a myocardial infarction in a patient having or at risk for developing a myocardial infarction. The method involves administering to the patient a therapeutically effective amount of an agent that restores a PDGF AB dependent communication pathway.

The invention also provides a method for reducing the size of a myocardial infarction in a patient at risk for developing a myocardial infarction, such a method can include administering to the patient a therapeutically effective amount of an agent that restores a PDGF AB dependent communication pathway. The size of the myocardial infarction can be measured by the extent of myocardial necrosis.

The invention also provides a method of restoring cardiac angiogenic function in a patient having senescent cardiac angiogenic function. Such a method can include administering to the patient a therapeutically effective amount of an agent that restores a PDGF AB dependent communication pathway.

The invention also provides a method of restoring vascular function in a patient having peripheral vasculature disorder (PVD), wherein the method comprises administering to the patient a therapeutically effective amount of an agent that restores a PDGF AB dependent communication pathway.

The invention further provides a method of restoring vascular function in or near the brain of a patient in need of such restoration, wherein the method comprises administering to the patient a therapeutically effective amount of an agent that restores a PDGF AB dependent communication pathway. The patient may be suffering or may have suffered a stroke.

The invention further provides a method of restoring cardioplastic potential of bone marrow cells obtained from a patient having senescent cardiac angiogenic function, wherein the method comprises administering an effective amount of PDGF AB to a culture of said bone marrow cells.

The invention also provides a method of treating cardiovascular dysfunction, wherein the method comprises administering to a patient suffering from said dysfunction, a therapeutically effective amount of cardiac myocytes, wherein said cardiac myocytes are derived from autologous stem cells and wherein said stem cells have been cultured in the presence of PDGF AB. The cardiovascular dysfunction can be at least one of myocardial infarction, ischemia, peripheral vasculature disorder (PVD), stroke, arrhythmia, tachycardia, or heart failure.

The invention further provides a method of restoring cardiac angiogenic function in a patient having senescent cardiac angiogenic function, wherein the method comprises administering to the patient a therapeutically effective amount of cardiac myocytes, wherein said cardiac myocytes are derived from autologous stem cells and wherein said stem cells have been cultured in the presence of PDGF AB.

The invention also provides a method of restoring cardioplastic potential of stem cells obtained from a patient having senescent cardiac angiogenic function, wherein the method comprises administering to a culture of said stem cells, an effective amount of PDGF AB.

The invention further provides a method of increasing the kinetics of cardiac myocyte derivation from bone marrow cells obtained from a patient having senescent cardiac angiogenic function, wherein the method involves administering to a culture of said bone marrow cells an effective amount of PDGF AB.

The invention also provides a method of increasing the kinetics of cardiac myocyte derivation from stem cells obtained from a patient having senescent cardiac angiogenic function, wherein the method comprises administering to a culture of said stem cells an effective amount of PDGF AB.

The agent that restores a PDGF AB dependent communication pathway can be at least one of PDGF AB, PDGF A, PDGF B, stem cells, young bone marrow endothelial precursor cells, epidermal growth factor or small molecule. The route of administration is by intravascular, intravenous, intraarterial, intraperitoneal, or intraventricular infusion, stem cell, infusion catheter, balloon catheter, bolus injection, direct application to tissue surfaces during surgery, oral or topical administration. The stem cells or young bone marrow endothelial precursor cells can be genetically modified to express a heterologous protein, RNA, or hormone. The stem cells or young bone marrow endothelial precursor cells can be genetically modified to over-express a native protein, RNA or hormone. The stem cells or young bone marrow endothelial precursor cells may also be modified to express, for example, cytokines, growth factors, hormones, signaling intermediates, sugar moieties, small molecules, anti-sense RNA, and to perform various biological actions that facilitate vascularization of senescent tissues.

The invention further provides cardiac myocytes exhibiting cardioplastic potential and derived from endothelial precursor cells obtained from a patient having senescent cardiac angiogenic function, said cardiac myocytes obtained through a process of culturing said endothelial precursor cell in the presence of an effective amount of PDGF, for example, PDGF AB or PDGF BB. Such endothelial precursor cells can be derived from bone marrow, peripheral blood, umbilical cord blood, organs, tissue, or fat.

The invention also provides a method of delivering platelet derived growth factor to cardiac tissues of a mammal comprising administering live endothelial precursor cells to a mammal and thereby delivering platelet derived growth factor to cardiac tissues. The platelet-derived growth factor can be PDGF B, PDGF A, PDGF AB, PDGF BB or any other form of PDGF that has activity or can combine with a PDGF polypeptide to generate an active PGDF protein.

The invention further provides a method of delivering platelet derived growth factor to cardiac tissues of a mammal comprising administering live young bone marrow cells to a mammal and thereby delivering platelet derived growth factor to cardiac tissues.

The invention also provides a method of preventing myocardial necrosis comprising administering live endothelial precursor cells to a mammal and thereby delivering platelet derived growth factor B to cardiac tissues in danger of myocardial necrosis.

The endothelial precursor cells and/or young bone marrow cells can express platelet-derived growth factor B upon association with cardiac myocytes within the cardiac tissues. Cardiac microvascular endothelial cells within the cardiac tissues can also express platelet-derived growth factor B after administration of the endothelial precursor cells and/or the young bone marrow cells. Such endothelial precursor cells and young bone marrow cells provide sustained delivery of platelet-derived growth factor B.

Administration of these cells can be intravascular, intravenous, intraarterial, intraperitoneal, via intraventricular infusion, via infusion catheter, via balloon catheter, via bolus injection, or via direct application to cardiac tissue during surgery. Administration can also be local or intravenous.

The endothelial precursor cells are derived from bone marrow, peripheral blood, umbilical cord blood, organs, tissue, or fat. Such endothelial precursor cells or young bone marrow cells can also be cultured in the presence of platelet derived growth factor AB prior to administration.

The cardiac tissues treated can be within a senescent heart. The mammal treated may have suffered from cardiovascular disease such as atherosclerosis, myocardial infarction, ischemia, tachycardia, or congestive heart failure.

DETAILED DESCRIPTION OF THE INVENTION

Figure 1:
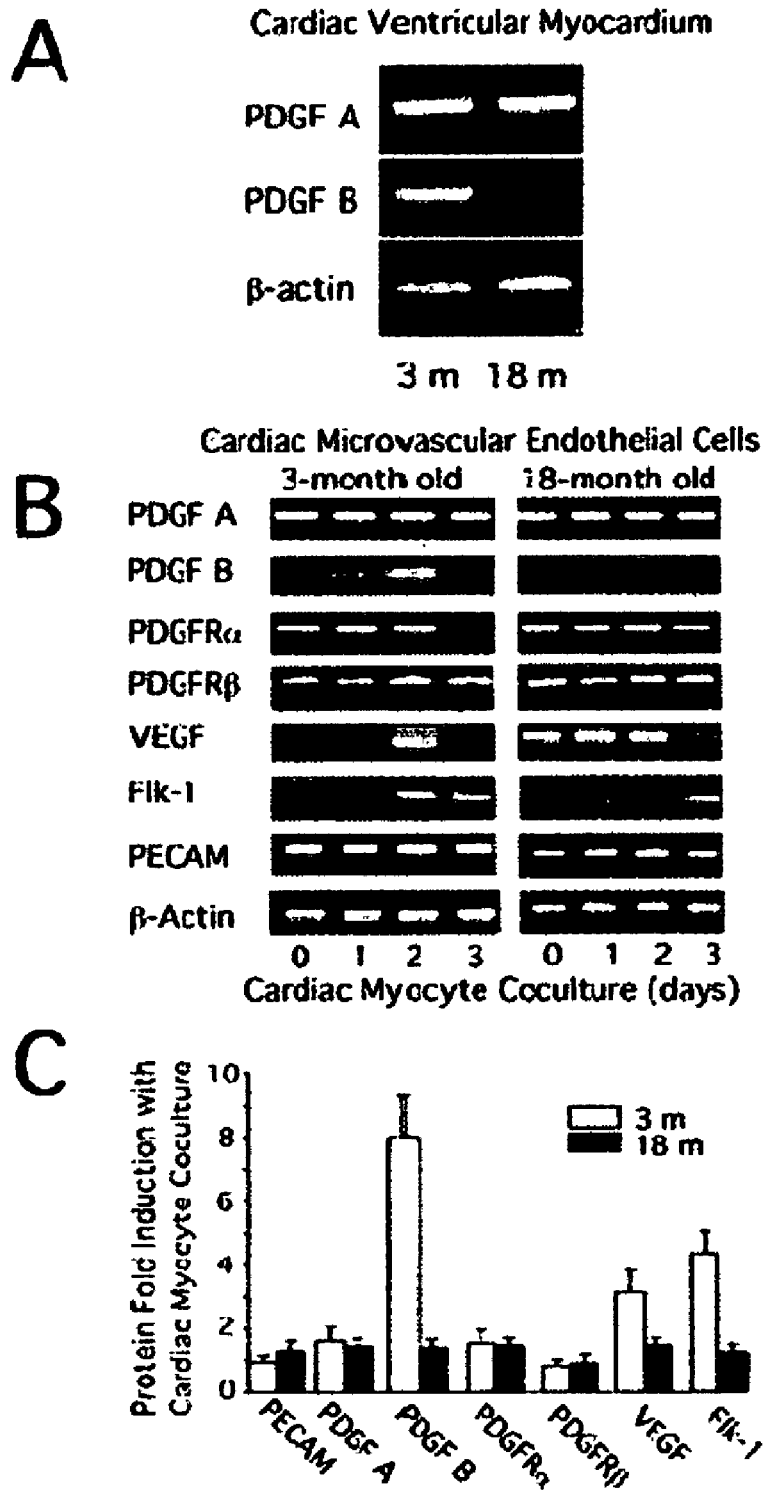
FIG. 1A provides a photograph of a gel illustrating an RT-PCR analysis of PDGF-A, PDGF-B, and β-actin expression in ventricular myocardial samples isolated from young adult (3 month) and senescent mice (18 month).
FIG. 1B provides a photograph of a gel illustrating the expression profile of CMECs from 3- and 18-month-old mice cocultured in transwells with fetal cardiac myocytes for zero to 3 days.
FIG. 1C provides a graph illustrating the fold-change in protein levels of CMECs from 3-month-old and 18-month-old mice cultured in the presence vs. the absence of fetal cardiac myocytes for 3 days.

The present invention provides pharmaceutical compositions comprising an effective amount of endothelial precursor cells, for example, young adult bone marrow cells. Such cells can be administered alone or in combination with platelet-derived growth factor (PDGF). Such administration can restore a PDGF dependent communication pathway that is dysfunctional in aging heart tissues, and can be utilized to treat vascular diseases and vascular injuries.

According to the invention, a PDGF dependent communication pathway comprises a series of cellular and biochemical events. Such a pathway involves cardiac myocytes that induce endothelial cells and endothelial precursor cells to express PDGF B. The PDGF B polypeptide can combine with PDGF A to generate PDGF AB. The PDGF AB protein can then stimulate endothelial cells that express the PDGFα receptor to express VEGF as well as FLK-1 and other genes. Overall, the induction of PDGF AB expression by endothelial cells or by endothelial precursor cells promotes angiogenic function. Some variations in this pathway exist. For example, a PDGF BB dimer can form that has activity. Hence, the PDGF BB dimer can also stimulate endothelial cells to express VEGF, FLK-1 and other genes.

As recognized by the invention, this PDGF dependent communication pathway is dysfunctional in the aging heart. "Dysfunctional" as used herein means that one or more steps in the PDGF dependent communication pathway are not functioning properly, for example, endothelial cells in the aging heart do not express PDGF B in the presence of cardiac myocytes. Accordingly, the invention provides methods of restoring PDGF B, PDGF AB and/or PDGF BB functions by delivery of exogenous growth factor or by recruitment of transplanted young bone marrow endothelial precursor cells can reverse the senescent impairment in cardiac angiogenic function.

Vascular Diseases

The vascular diseases treated by the present invention are vascular diseases of mammals. The word mammal means any mammal. Some examples of mammals include, for example, pet animals, such as dogs and cats; farm animals, such as pigs, cattle, sheep, and goats; laboratory animals, such as mice and rats; primates, such as monkeys, apes, and chimpanzees; and humans.

According to the invention, endothelial cells within normal vascular tissues change as they grow older, exhibiting reduced angiogenesis and losing their ability to communicate with other cells by secreting signaling agents. These changes can lead to a diminished capacity for blood vessel formation, a reduction in blood flow to the associated organ or system, and an inability to recover from injuries or diseases that adversely affect blood vessels.

Many pathological conditions can lead to vascular diseases such as atherosclerosis, preeclampsia, peripheral vascular disease, erectile dysfunction, cancers, renal failure, heart disease, and stroke. Such conditions are associated with alterations in the normal vascular condition of the affected tissues and/or systems.

Accordingly, this invention relates to methods for treating endothelial dysfunction or a vascular condition or a circulatory condition, such as a condition associated with loss, injury or disruption of the vasculature within an anatomical site or system. The term "vascular condition" or "vascular disease" refers to a state of vascular tissue where blood flow is, or can become, impaired.

Examples of vascular conditions or vascular disease to which the methods of the invention apply are those in which the vasculature of the affected tissue or system is senescent or otherwise altered in some way such that blood flow to the tissue or system is reduced or in danger of being reduced. Vascular, circulatory or hypoxic conditions to which the methods of the invention apply are those associated with, but not limited to, maternal hypoxia (e. g. , placental hypoxia, preeclampsia), abnormal pregnancy, peripheral vascular disease (e. g., arteriosclerosis), transplant accelerated arteriosclerosis, deep vein thrombosis, erectile dysfunction, cancers, renal failure, stroke, heart disease, sleep apnea, hypoxia during sleep, female sexual dysfunction, fetal hypoxia, smoking, anemia, hypovolemia, vascular or circulatory conditions which increase risk of metastasis or tumor progression, hemorrhage, hypertension, diabetes, vasculopathologies, surgery (e. g., per-surgical hypoxia, post-operative hypoxia), Raynaud's disease, endothelial dysfunction, regional perfusion deficits (e.g., limb, gut, renal ischemia), myocardial infarction, stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and Erythroblastosis (blue baby syndrome). In particular embodiments, the invention is a method of treating loss of circulation or endothelial dysfunction in an individual.

Thus, the invention is directed to methods of treating diseases such as stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), or thrombosis.

In some embodiments, the vascular condition or vascular disease arises from damaged myocardium. As used herein "damaged myocardium" refers to myocardial cells that have been exposed to ischemic conditions. These ischemic conditions may be caused by a myocardial infarction, or other cardiovascular disease. The lack of oxygen causes the death of the cells in the surrounding area, leaving an infarct that can eventually scar.

Preferably, damaged myocardium is treated with the methods and compositions of the invention before damage occurs (e.g.when damage is suspected of occurring) or as quickly as possible after damage occurs. Hence, the methods and compositions of the invention are advantageously employed on aged heart tissues that are in danger of ischemia, heart attack or loss of blood flow. The methods and compositions of the invention are also advantageously employed on recently damaged myocardium and on not so recently damaged myocardium.

As used herein "recently damaged myocardium" refers to myocardium that has been damaged within one week of treatment being started. In a preferred embodiment, the myocardium has been damaged within three days of the start of treatment. In a further preferred embodiment, the myocardium has been damaged within 12 hours of the start of treatment.

The methods and compositions of the invention can be used to prevent or to treat these vascular conditions. These methods involve administering an effective amount of endothelial precursor cells, for example, young bone marrow cells or young cardiac microvascular endothelial cells. Such cells can be administered alone or in combination with platelet-derived growth factor (PDGF). Such an effective amount is effective when it restores a PDGF AB dependent communication pathway that is dysfunctional in a tissue, for example, an aging heart tissue. In other embodiments, an effective amount is effective in that it stimulates the generation of myocytes or restores some vascularization in a tissue.

Endothelial Precursor Cells

According to the invention, endothelial precursor cells can reverse age-related defects in cardiac angiogenesis. These cells can restore and stimulate cardiac angiogenesis in an aging host, for example, by generating cardiac myocytes. These endothelial precursor cells can be stem cells, but need not be derived from embryos or fetuses. Instead, the endothelial precursor cells can be young adult bone marrow-derived cells, and/or adult stem cells.

Pluripotent stem cells are capable of developing into more than two types of mature cells, such as endothelial cells, hematopoictic cells, and at least one other type of cells. Bipotent stem cells are capable of developing into two types of mature cells, such as endothelial cells and hematopoietic cells. Progenitor cells are capable of developing into one type of mature cells, such as endothelial cells or hematopoietic cells. Pluripotent stem cells, bipotent stem cells, and progenitor cells are capable of developing into mature cells either directly, or indirectly through one or more intermediate stem or progenitor cells. An endothelial stem cell is a stem cell that is capable of maturing into at least one type of mature endothelial cell. The endothelial stem cell may be pluripotent, bipotent, or monopotent. Monopotent endothelial stem cells are also referred to as endothelial progenitor cells Pluripotent endothelial stem cells are capable of developing into mature endothelial cells and at least two other types of cells. Bipotent endothelial stem cells are capable of developing into mature endothelial cells and one other type of cells, such as hematopoietic cells. Monopotent endothelial cells, i.e. endothelial progenitor cells, are capable of developing into mature endothelial cells.

Accordingly to the above definitions, the term endothelial precursor cells always includes progenitor cells that can stimulate production of myocytes. However, any population of stem cells (pluripotent, bipotent, monopotent, etc.) or precursor cell types can be used in the invention so long as they can generate myocytes.

Endothelial precursor cells can be identified by their surface antigens and/or by the factors they express. Such antigens include, for example, one or more vascular endothelial growth factor receptors (VEGFR). Examples of VEGFRs include FLK-1 and FLT-1. The FLK-1 receptor is also known by other names, such as VEGFR-2. Human FLK-1 is sometimes referred to in the literature and herein as KDR.

At least some endothelial precursor cells also express the CD34+ marker. The endothelial precursor cells may be further characterized by the absence or significantly lower expression levels of certain markers characteristic of mature cells. Such markers include CD1, CD3, CD8, CD10, CD13, CD14, CD15, CD19, CD20, CD33, and CD41A.

In addition, at least some endothelial precursor cells also express the AC 133 antigen, which was described by Yin et al. in Blood 90, 5002-5112 (1997) and by Miraglia et al. in Blood 90, 5013-5021 (1997). The AC133 antigen is expressed on endothelial and hematopoietic precursor cells, but not on mature cells.

Most, if not all, of the endothelial precursor cells express FLK-1. The CD34 marker is characteristic of precursor cells, such as angioblasts and hematopoietic precursor cells. Approximately 0.5-10% of CD34+ cells are also FLK-1+. For example, approximately 1% of bone marrow cells are CD34+. Of these, approximately 1% are FLK-1+.

The source of cells from which isolated endothelial precursor cells are derived may be any natural or non-natural mixture of cells that contain endothelial precursor cells. The source may be derived from an embryo, or from the post-natal mammal. Preferably, the source of cells is the hematopoietic microenvironment, such as the circulating peripheral blood, preferably from the mononuclear fraction of peripheral blood, umbilical cord blood, bone marrow, fetal liver, or yolk sac of a mammal. The source of cells therefore need not be embryonic or fetal.

In one embodiment, the method relates to a method of isolating endothelial precursor cells that can be used to generate myocytes in living heart tissue. The population of endothelial precursor cells may be purified. However, no such purification is needed so long as no adverse immunological reaction will occur upon administration to a mammal. By purified is meant that the population is significantly enriched in endothelial precursor cells from the crude population of cells from which the endothelial precursor cells are isolated.

For example, the purification procedure should lead at least to a five fold increase, preferably at least a ten fold increase, more preferably at least a fifteen fold increase, most preferably at least a twenty fold increase, and optimally at least a twenty-five fold increase in endothelial precursor cells over the total population. The purified population of endothelial precursor cells should include at least 15%, preferably at least 20%, more preferably at least 25%, most preferably at least 35%, and optimally at least 50% of endothelial precursor cells.

The methods described in this specification can lead to mixtures comprising up to 75%, preferably up to 80%, more preferably up to 85%, most preferably up to 90% and optimally up to 95% of endothelial precursor cells. Such methods are capable of producing mixtures comprising 99%, 99.9% and even 100% of endothelial precursor cells. Accordingly, the purified populations of the invention contain significantly higher levels of endothelial precursor cells than those that exist in nature, as described above.

A population of endothelial precursor cells can be isolated from bone marrow. Isolated cells are not necessarily pure cells; instead, isolated cells are removed from their natural source, environment or from the mammal where they naturally arose. Endothelial precursor calls can be isolated from a population of bone marrow cells by extracting them or removing them from the bone marrow.

Endothelial precursor cells can be identified by observing their expression patterns or by contacting the cells with a molecule that binds specifically to the extracellular portion of an antigen specific for endothelial precursor cells. The binding of the endothelial precursor cells to the molecule permits the endothelial precursor cells to be sufficiently distinguished from contaminating cells that do not express the antigen to permit isolating the endothelial precursor cells from the contaminating cells. The antigen can be VEGFR, or FLK-1. In a preferred embodiment, the marker is PDGF B or CD34.

The molecule used to separate endothelial precursor cells from the contaminating cells can be any molecule that is specifically expressed within the endothelial precursor cells or that binds specifically to the antigen that characterizes the endothelial precursor cell. The molecule can be, for example, a monoclonal antibody, a fragment of a monoclonal antibody, or, in the case of an antigen that is a receptor, the ligand of that receptor. For example, in the case of a VEGF receptor, such as FLK-1, the ligand is VEGF. Other molecules that can be used to separate endothelial precursor cells from other cells include PDGF alpha receptor, VEGF-1 receptor, VEGF-2 receptor, VEGF-3 receptor, VEGF A, VEGF B, VEGF C, VEGF D, VEGF E, EGF, EGF receptor; tumor necrosis factor alpha and tumor necrosis factor receptor.

Either before or after the crude cell populations are purified as described above, the cells may be further enriched in precursor cells by methods known in the art. For example, human endothelial precursor cells may be pre-purified or post-purified by means of an anti-CD34 antibody, such as the anti-My-10 monoclonal antibody described by Civin in U.S. Pat. No. 5,130,144. The hybridoma cell line that expresses the anti-My monoclonal antibody is available from the American Type Culture Collection, 12301 Parklawn Drive, Rockville, Md. 20852, USA. Some additional sources of antibodies capable of selecting CD34+ cells include AMAC, Westbrook, Me.; Coulter, Hialea, Fla.; and Becton Dickinson, Mountain View, Calif. CD34+ cells may also be isolated by means of comparable antibodies, which may be produced by methods known in the art, such as those described by Civin in U.S. Pat. No. 5,130,144.

In addition, or as an alternative to, the enrichment with anti-CD34 antibodies, populations of endothelial precursor cells may also be further enriched with the AC133 antibodies described by Yin et al. in Blood 90, 5002-5112 (1997) and by Miraglia et al. in Blood 90,5013-5021 (1997). The AC133 antibodies may be prepared in accordance with Yin et al., ibid, or purchased from Miltenyi Biotec.

The preferred cells of the invention express PDGF B. Such cells may also express FLK-1, CD34, or AC133.

Suitable mixtures of cells from a hematopoietic microenvironment may be harvested from a mammalian donor by methods known in the art. For example, precursor endothelial cells may be isolated from bone marrow or from circulating peripheral blood. Endothelial precursor cells are mobilized (i.e., recruited) into the circulating peripheral blood by means of cytokines, such as, for example, G-CSF, GM-CSF, VEGF, SCF (c-kit ligand) and bFGF, chemokines, such as SDF-1, or interleukins, such as interleukins 1 and 8. Hence, endothelial precursor cells can be isolated from blood after recruiting those cells from bone marrow by pre-treatment with one or more of these cytokines. Alternatively, bone marrow may be obtained from a mammal, such as a human patient undergoing an autologous transplant.

The endothelial precursor cells can be identified within the mixture of cells obtained by exposing the cells to a molecule that binds specifically to the antigen marker characteristic of endothelial precursor cells. The molecule is preferably an antibody or a fragment of an antibody. A convenient antigen marker is PDGF, or a VEGF receptor, for example, a FLK-1 receptor. The cells that express the antigen marker bind to the molecule. The molecule distinguishes the bound cells from unbound cells, permitting separation and isolation. If the bound cells do not internalize the molecule, the molecule may be separated from the cell by methods known in the art. For example, antibodies may be separated from cells with a protease such as chymotrypsin.

The molecule used for isolating the purified populations of endothelial precursor cells is advantageously conjugated with labels that expedite identification and separation. Examples of such labels include magnetic beads, biotin, which may be removed by avidin or streptavidin, fluorochromes, which may be used in connection with a fluorescence-activated cell sorter, and the like.

Any technique may be used for isolation as long as the technique does not unduly harm the endothelial precursor cells. Many such methods are known in the art.

In one embodiment, the molecule is attached to a solid support. Some suitable solid supports include nitrocellulose, agarose beads, polystyrene beads, hollow fiber membranes, and plastic petri dishes.

For example, the molecule can be covalently linked to Pharmacia Sepharose 6MB macro beads. The exact conditions and duration of incubation for the solid phase-linked molecules with the crude cell mixture will depend upon several factors specific to the system employed, as is well known in the art.

Cells that are bound to the molecule are removed from the cell suspension by physically separating the solid support from the cell suspension. For example, the unbound cells may be eluted or washed away with physiologic buffer after allowing sufficient time for the solid support to bind the endothelial stem cells.

The bound cells are separated from the solid phase by any appropriate method, depending mainly upon the nature of the solid phase and the molecule. For example, bound cells can be eluted from a plastic petri dish by vigorous agitation. Alternatively, bound cells can be eluted by enzymatically "nicking" or digesting an enzyme-sensitive "spacer" sequence between the solid phase and an antibody. Suitable spacer sequences bound to agarose beads are commercially available from, for example, Pharmacia.

The eluted, enriched fraction of cells may then be washed with a buffer by centrifugation and preserved in a viable state at low temperatures for later use according to conventional technology. The cells may also be used immediately, for example by being infused intravenously into a recipient.

In a particularly preferred variation of the method described above, blood is withdrawn directly from the circulating peripheral blood of a donor. The blood is percolated continuously through a column containing the solid phase-linked molecule to remove endothelial precursor cells. The precursor cell-depleted blood is returned immediately to the donor's circulatory system by methods known in the art, such as hemapheresis. The blood is processed in this way until a sufficient number of precursor cells binds to the column. This method allows rare peripheral blood precursor cells to be harvested from a very large volume of blood, sparing the donor the expense and pain of harvesting bone marrow and the associated risks of anesthesia, analgesia, blood transfusion, and infection.

Other methods for isolating the purified populations of endothelial precursor cells are also known. Such methods include magnetic separation with antibody-coated magnetic beads, and "panning" with an antibody attached to a solid matrix.

Other methods for isolating the purified populations of endothelial precursor cells include general fluorescence activated cell sorting (FACS) protocols. In one embodiment, a labeled molecule is bound to the endothelial precursor cells, and the labeled cells are separated by a mechanical cell sorter that detects the presence of the label. The preferred mechanical cell sorter is a florescence activated cell sorter (FACS). FACS machines are commercially available. Generally, the following FACS protocol is suitable for this procedure:

A Coulter Epics Eliter sorter is sterilized by running 70% ethanol through the systems. The lines are flushed with sterile distilled water.

Cells are incubated with a primary antibody diluted in Hank's balanced salt solution supplemented with 1% bovine serum albumin (HB) for 60 minutes on ice. The cells are washed with HB and incubated with a secondary antibody labeled with fluorescein isothiocyanate (FITC) for 30 minutes on ice. The secondary label binds to the primary antibody. The sorting parameters, such as baseline fluorescence, are determined with an irrelevant primary antibody. The final cell concentration is usually set at one million cells per ml.

While the cells are being labeled, a sort matrix is determined using fluorescent beads as a means of aligning the instrument.

Once the appropriate parameters are determined, the cells are sorted and collected in sterile tubes containing medium supplemented with fetal bovine serum and antibiotics, usually penicillin, streptomycin and/or gentamicin. After sorting, the cells are re-analyzed on the FACS to determine the purity of the sort.

In another embodiment, the invention is directed to isolated populations of precursor cells that express a suitable marker, for example, PDGF B or a VEGF receptor, such as, for example, the FLK-1 receptor. This embodiment further includes isolation of purified populations of such cells. The PDGF B+ precursor cells include, for example, endothelial precursor cells. The source of cells from which the precursor cells are obtained include both pre-natal and post-natal sources. Post-natal sources are preferred.

Methods for Inducing Neovascularization

The invention is further directed to a method for inducing neovascularization in a mammal by treating the mammal with an effective amount of a population of endothelial precursor cells and/or a PDGF isoform. Neovascularization refers to the development of new blood vessels from endothelial precursor cells by any means, such as by vasculogenesis, angiogenesis, or the formation of new blood vessels from endothelial precursor cells that link to existing blood vessels.

Endothelial precursor cells may be pre-treated with cytokines and other factors, such as, for example, G-CSF, GM-CSF, VEGF, SCF (c-kit ligand) and bFGF, chemokines, such as SDF-1, or interleukins, such as interleukins 1 and 8. In some embodiments, endothelial precursor cells are pre-treated with such cytokines before administration to a mammal. According to the invention, PDGF isoforms can also stimulate endothelial precursor cells to generate myocytes. Therefore, in some embodiments, endothelial precursor cells are pre-treated with PDGF A, PDGF B, PDGF BB or PDGF AB before administration to a mammal. Preferably, the endothelial precursor cells are pretreated with PDGF AB.

Platelet-Derived Growth Factor

Naturally occurring, platelet-derived growth factor ("PDGF") is a disulfide-bonded dimer having two polypeptide chains, namely the "A" and "B" chains, with the A chain being approximately 60% homologous to the B chain. Naturally occurring PDGF is found in three dimeric forms, namely PDGF-AB heterodimer, PDGF-BB homodimer, or PDGF-AA homodimer. Hannink et al., Mol. Cell. Biol., 6, 1304-1314 (1986). PDGF-AB has been identified as a predominate naturally occurring form. However, some data indicates that the PDGF-BB homodimer may be effective for wound healing. Each monomeric subunit of the biologically active dimer, irrespective of whether it is an A chain monomer or a B chain monomer, contains eight cysteine residues. Some of these cysteine residues form interchain disulfide bonds that hold the dimer together. As used herein, the term PDGF means any PDGF polypeptide or protein, including PDGF A, PDGF B, PDGF AB, PDGF BB, and PDGF AA.

The A polypeptide of human PDGF can be any mammalian PDGF A polypeptide including, for example, human, mouse, rat, rabbit, goat, bovine, horse, sheep and any other mammalian PDGF A polypeptide. The following sequence is one example of an amino acid sequence of a human PDGF A polypeptide (SEQ ID NO:1):

```
  1 MRTWACLLLL GCGYLAHALA EEAEIPRELI ERLARSQIHS

41 IRDLQRLLEI DSVGAEDALE TNLRAHGSHT VKHVPEKRPV

81 PIRRKRSIEE AIPAVCKTRT VIYEIPRSQV DPTSANFLIW

121 PPCVEVKRCT GCCNTSSVKC QPSRVHHRSV KVAKVEYVRK

161 KPKLKEVQVR LEEHLECACA TSNLNPDHRE EETGRRRESG

201 KKRK
```

The following sequence is an example of a mouse PDGF A sequence (SEQ ID NO:2).

```
  1 MRTWACLLLL GCGYLAHALA EEAEIPRELI ERLARSQIHS

41 IRDLQRLLEI DSVGAEDALE TSLRAHGSHA INHVPEKRPV

81 PIRRKRSIEE AVPAVCKTRT VIYEIPRSQV DPTSANFLIW

121 PPCVEVKRCT GCCNTSSVKC QPSRVHHRSV KVAKVEYVRK

161 KPKLKEVQVR LEEDLECACA TSNLNPDHRE EETDVR
```

Other sequences for PDGF A can readily be obtained by one of skill in the art, for example, in the GenBank database of sequences. Variability in these and other sequences is permitted so long as the PDGF A polypeptide can dimerize with PDGF B and/or function in cell-to-cell communication.

The PDGF B polypeptide found in human platelets has been identified as a 109 amino acid cleavage product (PDGF-$B_{109}$) of a 241 amino acid precursor polypeptide Johnsson et al., EMBO Journal, 3(5), 921-928 (1984). An example of a human sequence for the PDGF B polypeptide is provided below (SEQ ID NO:3).

```
  1 MNRCWALFLS LCCYLRLVSA EGDPIPEELY EMLSDHSIRS

41 FDDLQRLLHG DPGEEDGAEL DLNMTRSHSG GELESLARGR

82 RSLGSLTIAE PAMIAECKTR TEVFEISRRL IDRTNANFLV

121 WPPCVEVQRC SGCCNNRNVQ CRPTQVQLRP VQVRKIEIVR

161 KKPIFKKATV TLEDHLACKC ETVAAARPVT RSPGGSQEQR

201 AKTPQTRVTI RTVRVRRPPK GKHRKFKHTH DKTALKETLG

241 A
```

The following sequence is an example of a mouse PDGF B sequence (SEQ ID NO:4).

```
  1 MNRCWALFLP LCCYLRLVSA EGDPIPEELY EMLSDHSIRS

41 FDDLQRLLHR DSVDEDGAEL DLNMTRAHSG VELESSSRGR

81 RSLGSLAAAE PAVIAECKTR TEVFQISRNL TDRTNANFLV
```

```
                       -continued
121 WPPCVEVQRC SGCCNNRNVQ CRASQVQMRP VQVRKIEIVR

161 KKPIFKKATV TLEDHLACKC ETIVTPRPVT RSPGTSREQR

201 AKTPQARVTI RTVRIRRPPK GKHRKFKHTH DKAALKETLG

241 A
```

As recognized by one of skill in the art, these PDGF polypeptides from different mammalian species have similar amino acid sequences. According to the invention any PDGF polypeptide from any mammalian species can be utilized in the practice of the invention so long as the PDGF polypeptide can stimulate endothelial cells to express VEGF and/or promote angiogenesis.

A 109 amino acid PDGF B polypeptide is believed to be the mature form of PDGF in humans and constitutes a cleavage product of the PDGF-B precursor protein. Homology with the precursor protein begins at amino acid 82 of the 241 amino acid precursor protein and continues for 109 amino acids yielding, for example, a polypeptide with the following sequence (SEQ ID NO:5):

```
 82 RSLGSLTIAE PAMIAECKTR TEVFEISRRL IDRTNANFLV

121 WPPCVEVQRC SGCCNNRNVQ CRPTQVQLRP VQVRKIEIVR

161 KKPIFKKATV TLEDHLACKC ETVAAARPVT RSPGGSQEQR

201 AKTPQTRVTI RTVRVRRPPK GKHRKFKHTH DKTALKETLG

241 A
```

Another form of PDGF-B (PDGF-$B_{119}$), corresponds to the first 119 amino acids of the PDGF-B precursor protein (SEQ ID NO:6):

```
  1 MNRCWALFLS LCCYLRLVSA EGDPIPEELY EMLSDHSIRS

41 FDDLQRLLHG DPGEEDGAEL DLNMTRSHSG GELESLARGR

82 RSLGSLTIAE PAMIAECKTR TEVFEISRRL IDRTNANFL
```

This PDGF-$B_{119}$ form has also been identified as a major cleavage product of the precursor protein when the entire gene is encoded into a transfected mammalian host. See U.S. Pat. No. 5,149,792.

Human platelet-derived growth factor is believed to be the major mitogenic growth factor in serum for connective tissue cells. PDGF can positively affect mitogenesis in arterial smooth muscle cells, fibroblast cells lines, and glial cells. Deuel et al., J. Biol. Chem., 256(17), 8896-8899 (1981). See also, e.g., Heldin et al., J. Cell Physiol., 105, 235 (1980) (brain glial cells); Raines and Ross, J. Biol. Chem., 257, 5154 (1982) (monkey arterial smooth muscle cells). PDGF is also believed to be a chemoattractant for fibroblasts, smooth muscle cells, monocytes, and granulocytes.

Other members of the PDGF family include vascular endothelial cell growth factor ("VEGF", sometimes also referred to as "vascular permeability factor, or "VPF") and placental growth factor ("PLGF"). Tischer et al., Biochem. Biophys. Res. Comm., 165(3), 1198-1206 (1989) and Maglione et al., Proc. Natl. Acad. Sci. USA, 88, 9267-9271 (1991), respectively. Both VEGF and PLGF form disulfide-bonded dimers from the eight highly conserved cysteine residues that appear in the PDGF homologous region of each monomeric unit of these PDGF family members. Tischer et al. and Maglione et al., ibid. The receptors for VEGF and PLGF are also in the same receptor subfamily as the PDGF receptors. Consequently, these "newer" members of the PDGF family are thought to be potentially useful as therapeutic products in wound repair, although they have not been studied as extensively as PDGF.

According to the invention, a platelet-derived growth factor-mediated communication exists between endothelial cells and myocytes. In the heart, cardiac microvascular endothelial cells (CMECs) communicate with neighboring cardiac myocytes via PDGF. Cardiac myocytes induce CMECs to express the PDGF B isoform that combines with the constitutively expressed PDGF A isoform to form the PDGF AB heterodimer. This results in the induction of a cascade of molecular events that maintain vascular integrity, including the endothelial expression of vascular endothelial growth factor (VEGF) and VEGF receptor-2 (Flk-1, VEGFR-2).

According to the invention, disruption of these angiogenic pathways may lead to angiogenic defects. One way that angiogenic pathways can be disrupted is by age-related alterations in cardiac PDGF levels.

Modulating PDGF-Dependent Pathways

According to the invention, PDGF dependent pathways can mediate the generation of cardiac myocytes from mammalian bone marrow. Precursor endothelial cells can supply PDGF to aging vascular tissues that have an impaired ability to generate new blood vessels. Young adult bone marrow-derived endothelial precursor cells can recreate a platelet-derived growth factor (PDGF)-mediated communication pathway between endothelial precursor cells and cardiac myocytes and thereby contribute to the generation of cardiac myocytes. While this pathway is required for cardiac vascular development and function, the pathway is lost or disrupted in older cardiac tissues and in older bone marrow. However, administration of PDGF and/or precursor endothelial cells can rescue the cardioplastic potential of the aging bone marrow.

As provided herein, PDGF isoforms can also help restore and stimulate cardiac myocyte generation. PDGF can be used to rejuvenate aging bone marrow from a mammal suffering from heart disease or some other vascular disease. When bone marrow is removed from older individuals, it cannot respond to myocytes and does not express PDGF B. However, when such older bone marrow cells are cultured with PDGF, those bone marrow cells begin to express PDGF B, and begin to generate cardiac myocytes. Use of PDGF isoforns enhances the speed at which cardiac myocytes are generated from all types of endothelial precursor cells. Use of an individual's own bone marrow avoids problems of cell typing, cell matching and the potential for immunological rejection of mismatched cells.

Therefore, the invention provides cardiac myocytes exhibiting cardioplastic potential that are derived from endothelial precursor cells obtained from a patient having senescent cardiac angiogenic function. These cardiac myocytes are obtained through a process of culturing the endothelial precursor cell in the presence of an effective amount of PDGF, for example, PDGF AB or PDGF BB. Such endothelial precursor cells can be derived from bone marrow, peripheral blood, umbilical cord blood, organs, tissue, or fat.

The invention further provides a method of treating a patient having senescent cardiac angiogenic function by administering endothelial precursor cells obtained from the patient having senescent cardiac angiogenic function, wherein the endothelial precursor cells were cultured in the presence of an effective amount of PDGF prior to administration. Such PDGF can be, for example, PDGF AB or PDGF BB. Such endothelial precursor cells can be derived from bone marrow, peripheral blood, umbilical cord blood, organs, tissue, or fat.

According to the invention, the actions of PDGF extend beyond the direct regulation of blood vessels and are critical in establishing and/or maintaining an environment that permits the generation of cardiac myocytes from bone marrow stem cells. The senescent impairment in cardiac myocyte-endothelial-PDGF-B expression pathway diminishes the systemic capacity to generate myocardial cells for the aging heart and contributes to the increased pathogenesis of cardiovascular disease in older persons. Since PDGF-AB enhances the generation of cardiac myocytes of bone marrow cells of all age groups, the critical downstream pathways in the precursor cells from the senescent bone marrow are likely to be intact.

Platelet-derived growth factor (PDGF) AB-mediated communication exists between cardiac microvascular endothelial cells (CMECs) and the neighboring cardiac myocytes. Cardiac myocytes induce CMECs to express the PDGF B isoform that combines with the constitutively expressed PDGF A isoform to form the PDGF AB heterodimer. This results in the induction of a cascade of molecular events that maintain vascular integrity, including the endothelial expression of vascular endothelial growth factor (VEGF) and VEGF receptor-2 (Flk-1, VEGFR-2).

The present invention provides experiments demonstrating that aging-associated alterations in endothelial cells inhibit the induction of the PDGF B-dependent cardiac communication pathway that governs cardiac angiogenic function. Restoration of this pathway by administration of an exogenous growth factor such as PDGF AB, or transplantation of endothelial precursor cells specifically restored cardiac angiogenic function in the aging host, and provides methods and compositions for treatment of cardiovascular disease in older individuals. The present studies were performed in unirradiated, wild type aged mice demonstrating the potential utility of bone marrow endothelial precursor cells in reconstituting endothelial function in the intact vasculature without ablating the host bone marrow.

In other embodiments, the invention provides a method of delivering PDGF B to vascular tissues that includes administering an effective amount of endothelial precursor cells to a mammal. The precursor endothelial cells become localized in cardiac tissues, and other vascular tissues, and may release PDGF B to those tissues. Such release of PDGF may be sustained but need not be. A single dose of PDGF delivered by such cells may be sufficient. Administration provides a naturally functioning cell type that may only need to be administered once or twice to generate myocytes and stimulate vascularization.

This invention provides methods for restoring senescent cardiac angiogenic function by administering bone marrow endothelial precursor cells that can, for example, be recruited from young bone marrow or from PDGF-treated older bone marrow. Transplantation of endothelial precursor populations offers novel means of delivering PDGF B and angio-competent endothelial cells to sites in need of angiogenesis.

Administration

Endothelial precursor cells may be administered in any manner so as to introduce the cells into the vascular system of the host. The cells may be introduced into a specific site in the vascular system to optimize delivery to a site that is known to have a vascular condition or disease. Such local delivery may avoid stimulation of inappropriate vascularization, for example, within a tumor that may be present in the mammal. However, endothelial precursor cells can find their way to diseased vascular tissues, so local administration may not be needed.

Endothelial precursor cells and/or bone marrow cells may be administered by intravascular, intravenous, intraarterial, intraperitoneal, intraventricular infusion, infusion catheter, balloon catheter, bolus injection, direct application to tissue surfaces during surgery, or other convenient routes. The cells can be washed after collection, cultured in an appropriate medium to insure their viability and to enhance their numbers. The cells can also be cultured in the presence of growth factors such as PDGF (e.g.PDGF AB), G-CSF, GM-CSF, VEGF, SCF (c-kit ligand), bFGF, chemokines such as SDF-1, or interleukins such as interleukins 1 and 8. Prior to administration, the cells can be washed again, for example, in buffered physiological saline.

The volume of cells that is injected and the concentration of cells in the transplanted solution depend on the site of administration, the vascular disease, and the species of the host. Preferably about one-half to about five microliters is injected at a time. The number of cells injected can vary, for example, about $10^2$ to about $10^{10}$ or about $10^4$ to about $10^9$ cells can be injected at one time. While a single injection may be sufficient, multiple injections may also be used.

Platelet derived growth factor isoforms can be administered with or without the endothelial precursor cells or young bone marrow cells of the invention. These PDGF polypeptides can therefore be incorporated into pharmaceutical compositions that also contain endothelial precursor cells or young bone marrow cells and that are suitable for administration to a mammal. Such compositions may also contain a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the cells or polypeptides provided herein, use thereof in the compositions is contemplated. Supplementary active compounds can also be incorporated into the compositions.

A pharmaceutical composition of the invention is formulated to be compatible with its intended route of administration. Examples of routes of administration include parenteral, intravenous, intradermal, subcutaneous, oral, inhalation, transdermal (topical), transmucosal, subdermal, subcutaneous, transdermal, or rectal. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PDGF B polypeptide or PDGF AB protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The PDGF and other compounds can also be prepared in the form of suppositories (e.g., with conventional suppository bases such as cocoa butter and other glycerides) or retention enemas for rectal delivery.

In one embodiment, the active compounds are prepared with carriers that will protect the PDGF polypeptides and other compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Sustained-release preparations can be prepared. Suitable examples of sustained-release preparations include semipermeable matrices of solid hydrophobic polymers containing the polypeptide(s), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release pharmaceutical active agents over shorter time periods.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active polypeptide and other compounds calculated to produce the desired therapeutic effect in association with the required pharmaceutical carrier.

The pharmaceutical compositions can be included in a kit, e.g., in a container, pack, or dispenser together with instructions for administration.

The following examples are intended to illustrate the invention and should not be interpreted to limit it in any manner.

EXAMPLE 1

Endothelial Precursor Cells Restore Angiogenesis

This Example provides data illustrating that endothelial dysregulation in the PDGF communication pathway underlies the impairment in senescent cardiac angiogenic potential and that young adult BM-derived endothelial precursor cells can reverse this defect and restore cardiac angiogenesis in the aging host.

Methods

Molecular Studies

Samples of the ventricular myocardium were isolated from 3 month old (n=3) and 18 month old C57B61/L mice (n=3). Total RNA was isolated (RNeasy and QIAshedder kits, Qiagen Valencia Calif.) and analyzed by RT-PCR (Hotstar Taq PCR, Qiagen) for expression of PDGF A and PDGF B as well as β-actin. Cardiac microvascular endothelial cells (CMECs) were isolated from 3 month old and 18 month old C57B61/L mice and cardiac myocytes from fetal murine hearts, as previously described. Edelberg et al. *J Clin Invest*. 1998: 102:837-43; Aird et al. *J. Cell Biol*. 1997: 138: 1117-24; Edelberg et al. *J Clin Invest*. 1998: 101: 337-43. These CMECs were then cultured in DMEM supplemented with 5% fetal calf serum, 20 U/mL heparin, 1% BME vitamins, 5 μg/mL insulin, 5 μg/mL transferrin, 5 ng/mL selenium, 100 μg/mL streptomycin, and 500 μg/mL penicillin, 4 μg/mL endothelial growth factor and 1% endothelial cell growth supplement (all from Sigma, St. Louis Mo.).

Bone marrow (BM) endothelial precursor cells were isolated from 3 and 18 month old mice as previously described. Lin et al. *J Clin Invest*. 2000;105:71-77. These BM endothelial precursor cells were then cultured in DMEM supplemented with 10% fetal calf serum, and 50 μg/mL heparin, 100 μg/mL streptomycin, and 500 μg/mL penicillin (all from Sigma) and 10 ng/mL vascular endothelial cell growth factor, 5 ng/mL fibroblast growth factor-2 (R & D Systems, Minneapolis Minn.). The endothelial cell cultures were expanded for two passages, confirmed by Di-Ac-LDL uptake and PECAM staining, and then plated into 12 well dishes ($10^5$ cell/well) (Costar, Cambridge Mass.).

Fetal cardiac myocytes (E15.5d) were isolated and plated in 12 mm 0.4 μm pore transwells ($10^5$ cell/transwell) and then were transferred at different time points (0 to 48 hours) into 3-month and 18-month old bone marrow-derived endothelial precursor cells seeded wells as described in Edelberg et al. 2002 *Circulation* 105:608-13 and Edelberg et al. *J Clin Invest*. 1998;102:837-43. As controls, cardiac microvascular endothelial cells were also isolated from 3-month and 18-month old C57B61/L mice and were cultured alone and with fetal cardiac myocytes for 48 hours as described in Edelberg et al. 2002 *Circulation* 105:608-13. At the termination of the co-culture total RNA was isolated from the endothelial cell wells and RT-PCR was performed. The following sets of oligonucleotide primers were employed:

```
mouse PDGF A:
(forward):
5'TCAAGGTGGCCAAAGTGGAG3'          (SEQ ID NO:7)
(reverse):
5'CTCTCTGTGACAAGGAAGCT3'          (SEQ ID NO:8)

mouse PDGF B:
(forward):
5'ATCGCCGAGTGCAAGACGCG3'          (SEQ ID NO:9)
(reverse):
5'AAGCACCATTGGCCGTCCGA3'          (SEQ ID NO:10)

mouse PDGFRα
(forward):
5'ACAGAGACTGAGCGCTGACA3'          (SEQ ID NO:11)
(reverse):
5'TTCCAAGAAGGAAGGAAGCA3'          (SEQ ID NO:12)
```

```
-continued
mouse VEGF-164:
(forward):
5'GGATCCATGAACTTTCTGCTGCTGTCTTGG3'    (SEQ ID NO:13)
(reverse):
5'TTCTGGCTTTGTCCTGTCTTTCTTTGG3'       (SEQ ID NO:14)

mouse Flk-1:
(forward):
5'CAGCTTGCTCCTTCCTCATC3'              (SEQ ID NO:15)
(reverse):
5'TCTGGAGAGCAAACCAACCA3'              (SEQ ID NO:16)

mouse von Willebrand Factor
(forward):
5'TGTCCAAGGTCTGAAGAAGA3'              (SEQ ID NO:17)
(reverse):
5'CAGGACAAACACCACATCCA3'              (SEQ ID NO:18)

mouse PECAM
(forward):
5'CAAGCGGTCGTGAATGACAC3'              (SEQ ID NO:19)
(reverse):
5'CACTGCCTTGACTGTCTTAAG3'             (SEQ ID NO:20)

mouse β-actin
(forward)
5'GTGGGCCGCTCTAGGCACCAA 3'            (SEQ ID NO:21)
(reverse)
5'CTCTTTGATGTCACGCACGATTTC3'          (SEQ ID NO:22)
```

Cellular and secreted protein samples were isolated from additional endothelial cell cultures in the presence or absence of fetal cardiac myocytes as previously described. Edelberg et al. *J Clin Invest.* 1998;102:837-43. Secreted samples (50 μl) from endothelial cells cultured alone or in the presence of cardiac myocytes were applied to Nunc maxisrop plates (Roskilde, Denmark) for 1 hour at room temperature. The samples were then washed with PBS 3 times, followed by blocking with 5% casein in PBS. Polyclonal antibodies to PDGF A (1:500, sc-128 Santa Cruz Biotechnology, Santa Cruz Calif.) and B, (1:300 dilution sc-7878, Santa Cruz Biotechnology), VEGF (1:200, AF 493-NA, R&D Systems), were then employed. Cellular lysate samples (50 μL) were assayed with antibodies directed against Flk-1 (1:500, AF 644, R&D Systems), PDGFRα (1:200, AF322, R&D Systems), and PECAM (1:500 dilution 550274, BD Pharmigen San Diego Calif.). After washing with PBS three times the plates were developed with peroxidase-labelled donkey polyclonal antibodies to goat, rabbit, and rat IgG (1:1000, Jackson Immunoresearch Laboratories, West Grove Pa.) and assayed as previously described. Edelberg et al. *J Clin Invest.* 1998; 102:837-43. All studies were performed a minimum of 3 times.

Cardiac Allografts Transplant Studies

Cardiac angiogenic potential was measured employing a cardiac allograft model transplanting a neonatal C57B61/L (24 hr old) murine heart into the pinnae of both syngeneic young adult (3 month old) and senescent (18 month old) murine hosts as described in Aird et al. *J. Cell Biol.* 1997: 138: 1117-24; Edelberg et al. *J Clin Invest.* 1998: 101: 337-43. The recipient mice were anesthetized with Avertin 2.5% (vol/vol) IP. After cleaning the dorsum of the pinna of the mouse ear with 70% ethanol, an incision penetrating only the epidermis, 2-5 mm in length, was made with a scalpel transverse to the longitudinal axis of the ear, 3-4 mm distal to its base on the skull. A small pocket between the skin and cartilage was then dissected with delicate curved forceps. The total donor neonatal heart was excised without the pericardial sac and inserted into the ear pocket. Gentle pressure with the tips of the forceps was applied to the ear to express air from the pocket and facilitate the adherence between donor and recipient tissues (n=20 3 month old, n=17 18 month old).

As controls, senescent mice were transplanted with inert silicon ($1\times1\times2$ mm$^3$) (n=8) or neonatal pulmonary allografts (n=8) in place of the neonatal cardiac tissue. In addition, sets of senescent hosts were pretreated with subcutaneous pinnal injections of recombinant VEGF (R&D Systems; 100 ng/20 μL PBS) (n=12), recombinant PDGF AB (R & D Systems; 100 ng/20 μL PBS) (n=12) or vehicle alone (n=8) 1 day prior to receiving cardiac allograft transplants. In addition, at the time of cardiac or pulmonary allograft transplantation sets of young adult mice were also treated with single subcutaneous pinnal injections of antibodies to neutralize PDGF AB (10 μg in 20 μL PBS, AB-20-NA, R&D Systems; n=8 cardiac, 8 pulmonary allografts) or nonimmune control rabbit IgG (10 μg in 20 μL PBS, AB-105-C, R&D Systems; n=8 cardiac, 8 pulmonary allografts). Allograft viability was scored by pinnal and transplant integrity. In addition, pinnal electrocardiograms were recorded as previously described to further document the viability of the cardiac allografts. Edelberg et al. *J Clin Invest.* 1998: 101: 337-43.

Auricular Angiogenesis Studies

Young adult (3 month old) and senescent mice (18 month old) received mid-pinnal injections of PDGF AB (100 ng/20 μL PBS) or PBS alone (n=8 for each group). Two days later the blood flow through both the middle and posterior auricular arteries was surgically interrupted by severing the base of the ear, thereby rendering the posterior auricular arterial circulation dependent on collateral flow from the intact anterior auricular artery, as previously described. Baker et al. 1999 *Br. J. Plast. Surg.* 52: 133-42. The functional blood flow to the posterior vascular bed was then assessed by laser Doppler with an Advance Laser Flowmeter ALF21/21D (Advance, Tokyo) as previously described. Rendell et al. 1998 *Microvasc. Res.* 55: 3-13.

Following completion of the rheology studies, the mice received intracardiac injections of lysine-fixable biotinylated-dextran ($2\times10^6$ M.W.; 50 μL of $10^{-5}$ M in PBS; Molecular Probes, Eugene Oreg.) to stain the perfused vasculature. Samples were fixed by 4% paraformaldehyde in PBS and then incubated with streptavidin-horse radish peroxidase and then developed with DAB. Histological measurements were performed with digital microscopy to assess functional vascular density of the posterior auricular vasculature as previously described. Thurston et al. 1999 *Science* 286: 2511-14.

Bone Marrow Transplantation

Bone marrow transplantation was performed as previously described. Spangrude et al. 1988 *Science* 241: 58-62. Briefly, 3 and 18 month old C57B 1/6 mice, as well as 3-month-old B6.129S7-Gtrosa26 (Rosa-26) mice were used. Friedrich et al. 1991 *Genes Dev.* 5: 1513-23. These mice were sacrificed and tibias and femurs were removed and trimmed of muscle and extraossial tissue. All the cells in the Rosa-26 express LacZ, therefore transplantation of the Rosa-26 bone marrow into the wild-type isogeneic senescent hosts facilitated the identification of the transplanted cells by X-gal staining. The bones were cut proximally and distally, and the bone marrow flushed with 2% bovine serum albumin in PBS. The cellular pellets were washed with and resuspended in PBS. The bone marrow cells were then injected into intact, unirradiated wild-type 18-month-old host C57B1/6 mice by tail vein injection with 300 μL of cells (3 month old C57B1/6: $10^7$ cells, n=16; $10^6$, n=12; $10^5$, n=6; 18 month old C57B1/6, $10^7$, n=6; 3 month old Rosa-26, $10^7$, n=6). The survival rates of all mice transplanted with exogenous bone marrow was 100%. One week after bone marrow transplantation the mice received pinnal cardiac allografts as described above. Seven day later mice receiving Rosa-26 bone marrow were sacrificed and the bone marrow and exogenous cardiac tissue with surrounding pinnal tissue were sectioned and stained for β-galactosidase activity as well as von Willebrand factor as previously described. Aird et al. *J. Cell Biol.* 1997: 138: 1117-24.

Results

Induction of PDGF B is Impaired in Senescent Endothelial Cells

RT-PCR analysis revealed that PDGF A was expressed in ventricular myocardial samples from both the young adult and senescent heart. See FIG. 1A. PDGF B expression, however, was detected only in young adult cardiac samples (FIG. 1A) suggesting that endothelial expression of PDGF B may be down regulated in the senescent heart.

Cardiac endothelial cells were isolated from both 3 and 18 month old wild-type mice and then co-cultured in the presence of fetal cardiac myocytes by using the transwell procedure described above. Endothelial cells of both young and senescent hearts constitutively expressed PDGF A. See FIGS. 1A and B. PDGF α-receptor (PDGFRα) was also expressed in the endothelial cells from both the young adult and senescent hearts. See FIGS. 1B and 1C. However, only the young adult CMECs expressed PDGF B in the presence of the fetal cardiac myocytes. See FIG. 1B. A significant increase in protein levels of PDGF B was observed in CMECs from 3-month-old hearts but not from 18-month-old hearts. See FIGS. 1B and 1C.

In addition to the differences in PDGF B expression, the expression pattern of other pro-angiogenic genes was also altered in the CMECs from aging mice. See FIGS. 1B and C. Unlike the young adult CMECs in which VEGF was induced in the co-culture with the cardiac myocytes, the senescent heart-derived endothelial cells expressed VEGF when cultured in isolation. However, VEGF mRNA levels decreased in senescent CMEC when cardiac myocytes were present. Furthermore, the expression of Flk-1 (VEGFR-2), the principal mitogenic receptor for VEGF, was significantly reduced in the senescent cells. Collectively, these results suggest that a disruption in cell-to-cell communication may be a primary defect in the aging heart. In particular, aging CMECs do not appear to respond to cardiac myocytes in the same manner as young CMECs.

PDGF AB Restores Cardiac Angiogenesis in Pinnal Allograft

Transplants

The potential functional significance of the dysregulation in cell-to-cell communication within senescent mouse heart tissues was then examined. These studies employed a syngeneic neonatal murine cardiac allograft-pinnal transplant model. Aird et al. *J. Cell Biol.* 1997: 138: 1117-24. This model effectively recreates the organ bed specific regulation of endothelial cells recruited from host peripheral vascular beds (id.). In these studies, endogenous PDGF AB was either neutralized by injection of anti-PDGF AB antibodies or enhanced by addition of exogenous PDGF AB.

Table 1 illustrates that neutralization of PDGF AB by injection of anti-PDGF AB into the pinnae of young mice at the time of transplantation significantly reduced the viability of cardiac allografts (3/8 viable vs. 8/8 viable with control antibody, p<0.05). The viability of pulmonary transplant engraftment was unaltered by neutralization of PDGF AB (8/8 viable vs. 8/8 viable with control antibody). Similarly, injection of anti-PDGFR-α antibodies at the time of transplantation significantly reduced cardiac allograft viability. Hence, PDGF AB and PDGFR-α are needed for survival of cardiac allografts. PDGFR-α is believed to be the major receptor that mediates the PDGF pathway, whereas PDGFR-β may have only a minor role.

TABLE 1

PDGF AB is Needed for Survival of Pinnal Cardiac Allograft Antibody Pretreatment

| Pinnal allograft | IgG | Anti-PDGF-AB | Anti-PDGFR-α | Anti-PDGFR-β |
|---|---|---|---|---|
| Heart viability | 9/9 | 3/8* | 3/7† | 7/7 |
| Lung viability | 8/8 | 8/8 | ND | ND |

IgG indicates immunoglobulin G;
ND, not determined.
*P__0.05 vs IgG heart and anti-PDGF-AB lung trials;
†P__0.05 vs IgG and anti-PDGFR-β heart trials.

Figure 2:
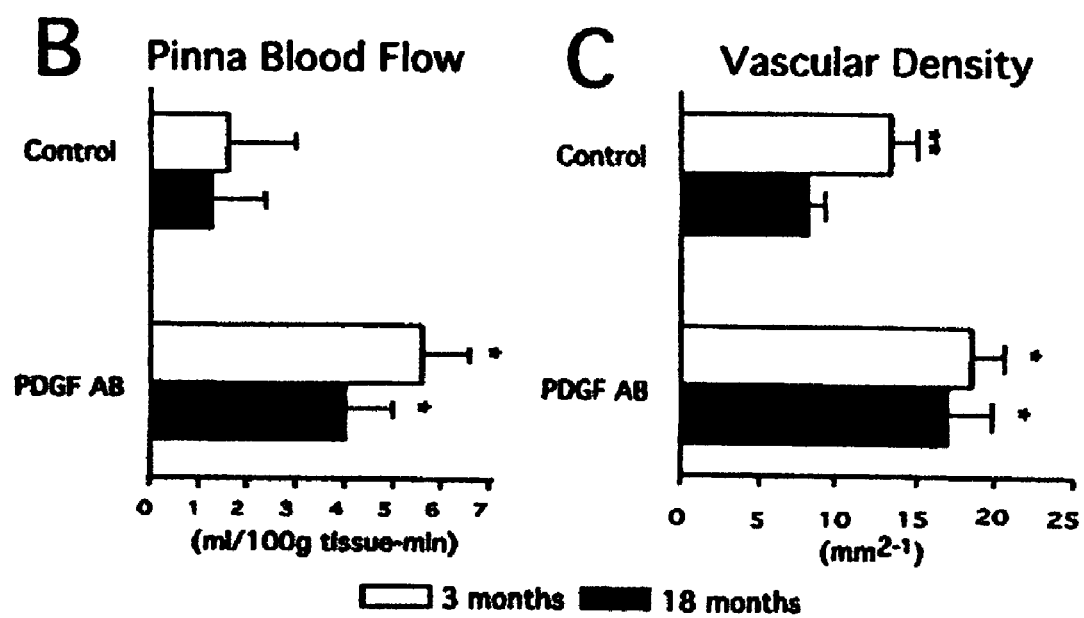
FIG. 2A provides representative examples of neonatal cardiac transplants into young adult (3 months old) (n=20) and senescent hosts (18 months old)(n=17). Senescent hosts were also transplanted with silicon (n=8), neonatal lungs (n=8), and neonatal hearts after pinnal pretreatment by injection of 100 ng of VEGF (n=12) or 100 ng of PDGF-AB (n=13). An arrow indicates viable/intact transplants. The majority of the cardiac allografts transplanted into the control and VEGF pretreated senescent mice resulted in a necrotic loss of both allograft and host pinnal tissue beyond the transplant site (arrowhead). Allograft viability was scored by pinnal and transplant integrity. Cardiac allograft viability in young adult and PDGF-AB-pretreated senescent hosts was confirmed by pinnal electrocardiograms (5-s tracing). *P<0.01 vs young adult; **P<0.01 vs senescent adult and P<0.01 vs senescent adult treated with VEGF.
FIG. 2B provides a bar graph illustrating pinnae blood in ml/100 g tissue/min in untreated tissues and in tissues treated with PDGF AB. These results were obtained by laser Doppler measurements of capillary blood flow in the posterior auricular circulation. Pretreatment with PDGF AB significantly increased blood flow in both the young (3 month) as well as the older (18 month) hosts.
FIG. 2C provides a bar graph illustrating vascular density per square mm in untreated tissues and in tissues treated with PDGF AB. These results were obtained by histological measurements of vascular density in the posterior auricular circulation. Histological assessment confirmed that PDGF AB increased collateral vascular density in the pinnae of both the young and senescent mice.
Figure 2A:

Cardiac allograft survival was markedly impaired in the aging mice as compared to the young adult mice. See FIG. 2A. However, wound healing was preserved in the older hosts, as demonstrated by the integrity of silicon implants. The viability of the pulmonary allografts suggested that the aging-associated changes were due to diminished senescent endothelial angiogenic function.

Various molecular mediators that were observed to be down regulated in senescent cardiac tissues were then tested to ascertain whether these molecules could restore cardiac angiogenic potential in aging mice. The subcutaneous pinnal administration of VEGF failed to improve the success of cardiac transplantation in the aging mice. See FIG. 2A. However, injection of PDGF AB into senescent implantation sites restored the viability of senescent allografts to that of the young adult hosts. See FIG. 2A. These data suggest that an aging-associated decrease in endothelial cell PDGF B gene expression underlies the impaired function in senescent cardiac angiogenic potential observed in vivo. Moreover, in these studies the PDGF B expressed in the transplanted tissue appeared to be insufficient to induce effective vascularization in the senescent hosts.

In order to define the mechanism mediating the restoration of senescent angiogenic function, the direct effects of PDGF AB pretreatment on the pinnal vasculature of the aged mice were tested. In particular, the development of functional blood vessels in both young adult and senescent mice was assessed using the murine cardiac allograft model, where induction of angiogenesis is essential for cardiac engraftment. Laser Doppler measurements demonstrated that pretreatment with PDGF AB significantly increased blood flow in both the young as well as older hosts. See FIG. 2B. In addition, histological assessment confirmed that the rheologic effects of PDGF AB were mediated by increasing collateral vascular density in the pinnae of both the young and senescent mice. See FIGS. 2B and 2C. These results suggest that PDGF AB restores the defects in senescent cardiac angiogenic function. Moreover, the auricular studies suggest that the PDGF AB rescue of the cardiac transplants is mediated by enhancing the vascular potential in the aging murine host.

Bone Marrow Endothelial Precursor Cells Restore Cardiac Angiogenic Function

Previous work suggested that some bone marrow-derived cells might be involved in post-natal angiogenesis. Shi et al. 1998 Blood 92: 362-67; Asahara et al. 1997 Science 275: 964-67; Kalka et al. 2000 Proc. Natl. Acad. Sci. U.S.A. 97:3422-27; Takahashi 1999 Nat. Med. 5: 434-38. Bone marrow endothelial precursor cells of young mice were tested to ascertain whether they could offer a novel means of restoring the PDGF-dependent angiogenic pathways in the aging vasculature. In particular, the capacity of young bone marrow endothelial precursor cells was tested to see whether they could reconstitute the critical cardiac myocyte-mediated PDGF regulatory pathways.

Figure 3:
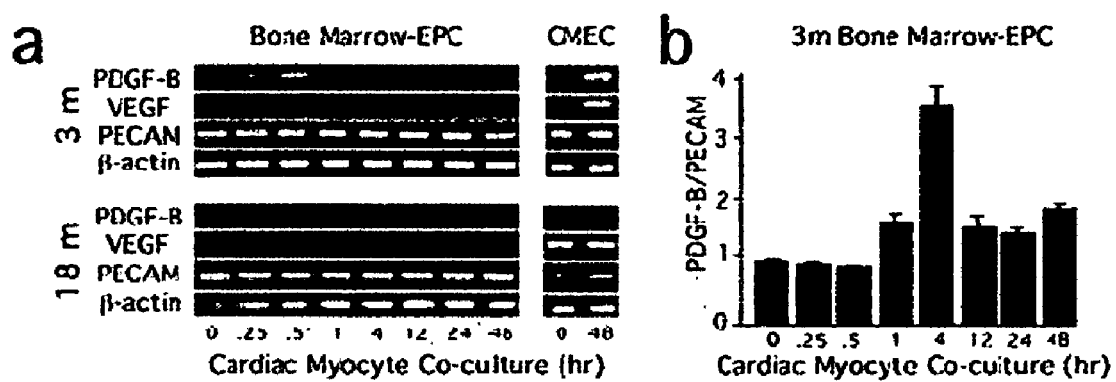
FIG. 3A illustrates the temporal gene expression profiles of bone marrow-derived endothelial precursor cells (EPCs) co-cultured for 0 to 48 hours with cardiac myocytes. By way of comparison, the temporal gene expression profiles of cardiac microvascular endothelial cells (CMECs) co-cultured for 0 and 48 hours with cardiac myocytes are shown. The top panels show the expression profiles of EPCs and CMECs isolated from 3-month-old mice, whereas the bottom panels show the expression profiles of EPCs and CMECs isolated from 18-month-old mice. As illustrated, the young EPCs and CMECs express PDGF B, whereas the older EPCs and CMECs do not.
FIG. 3B provides a graph illustrating the PDGF-B/PECAM protein ratio in 3-month-old bone marrow-derived EPCs that were cocultured with cardiac myocytes.
FIG. 3C provides representative photomicrographs of X-gal stained tissue sections from 18-month-old mice receiving $10^7$ bone marrow cells from 3-month-old Rosa-26 (β-galactosidase (+)) mice one week before cardiac engraftment. Aging wild-type host bone marrow with young transgenic cells (a), young transgenic cell incorporation in (b through e) and around (f and g) the wild-type cardiac myocardium transplanted into the aging hosts. Costaining for von Willebrand factor of intraallograft with arrows highlighting transgenic cells (c through e) and periallograft pinnal tissue (g) and for PDGF-B of intraallograft tissue (h); bar=25 μm (a,b, f, and g) and 10 μm (c, d, e, and h).
FIG. 3D provides representative examples of pinnal cardiac allografts in 18-month-old hosts with either no bone marrow transplantation (control) or $10^7$ bone marrow cells from 3-month-old donor (BMT) one week before cardiac engraftment. The arrow indicates the location of the viable cardiac allograft. The arrowhead provides the location of necrotic loss for both cardiac allograft and host pinnal tissue.
FIG. 3E provides a bar graph illustrating the viability of cardiac allografts in young and senescent control hosts (3-month-old, 8/8; 18-month-old, 1/8) and senescent hosts receiving bone marrow cells isolated from 18-month-old donors ($10^7$ cells, 0/6), and from 3-month-old donors ($10^5$ cells, 2/6; $10^6$ cells, 6/12; and $10^7$ cells, 15/16) alone or with pinnal antibody pretreatment (IgG, 7/7; anti-PDGF-AB, 3/7). *$P<0.05$ 3-month-old vs 18-month-old transplant hosts; $P<0.05$ 18-month-old hosts control vs transplantation with 3 month-old bone marrow; *$P<0.05$ IgG vs anti-PDGF AB.

FIGS. 3A and 3B show that PDGF B expression was induced in young bone marrow endothelial precursor cells and in young cardiac microvascular endothelial cells when these cells were co-cultured with cardiac myocytes. However, no such induction of PDGF B expression was observed in older bone marrow or cardiac microvascular endothelial cells. See FIG. 3A. PDGF B expression was induced in these young cells within about one hour of exposure to cardiac myocytes.

Figure 3C:
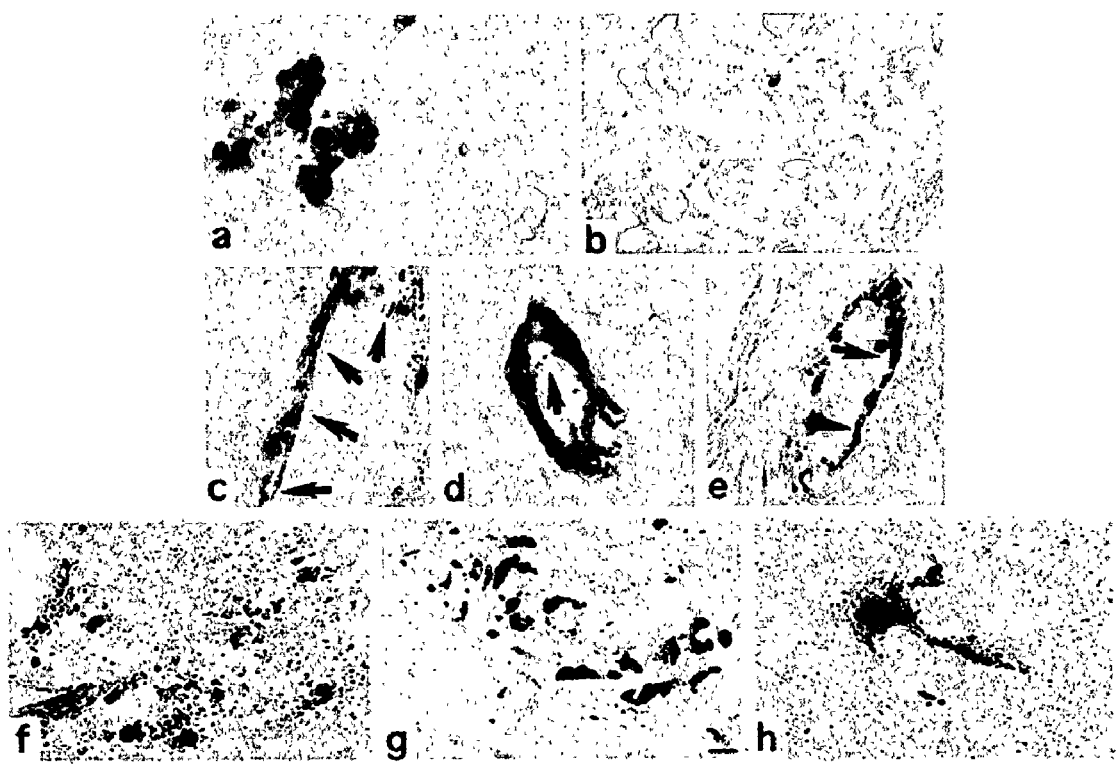

Bone marrow from young LacZ$^+$ Rosa-26 mice was then transplanted intravenously into intact, unirradiated older mice. Analysis of these mice revealed that β-galactosidase-positive cells were engrafted in the senescent (older) bone marrow. See FIG. 3C. FIG. 3C provides representative photomicrographs of X-gal stained tissue sections from 18-month-old mice that had received $10^7$ bone marrow cells from 3-month-old Rosa-26 (β-galactosidase (+)) mice one week before cardiac engraftment. The transplanted young bone marrow cells were incorporated both within and around the host cardiac myocardium (FIG. 3Cb-g). The bone marrow of older mice that had received young transgenic cells also stained positively for β-galactosidase (FIG. 3Ca). Cells within the allograft exhibited costaining with both von Willebrand factor and β-galactosidase (arrows highlight the transgenic cells in FIGS. 3Cc through e). vWF is a marker for cardiac myocyte-endothelial PDGF communication. Edelberg et al. *J Clin Invest*. 1998;102:837-43. Cells within the periallograft pinnal tissue also costained with both von Willebrand factor and β-galactosidase (FIG. 3Cg). Cells within the allograft also stained positively for PDGF-B (FIG. 3Ch). Hence, β-galactosidase-positive bone marrow endothelial precursor cells that co-stained with von Willebrand factor were recruited into the vascularization of the cardiac allografts in the peri- and intra-allograft microvasculature. See FIG. 3C(c-e,g). Bone marrow endothelial precursor cells that co-stained with β-galactosidase and PDGF-B were also recruited into the vascularization of the cardiac allografts in the intra-allograft microvasculature. See FIG. 3C(h).

Figure 3D:
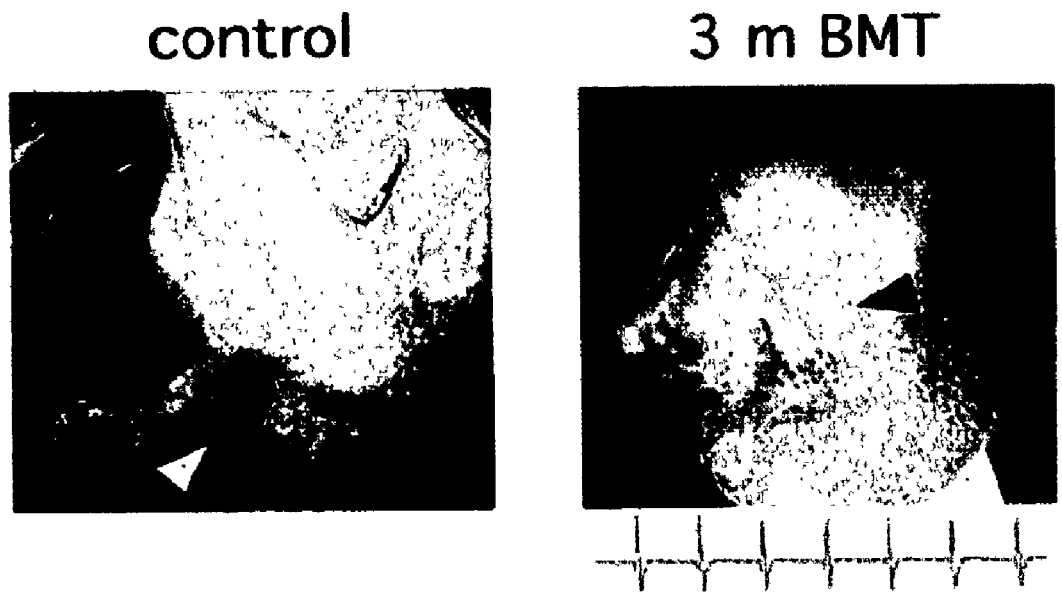
Figure 3E:
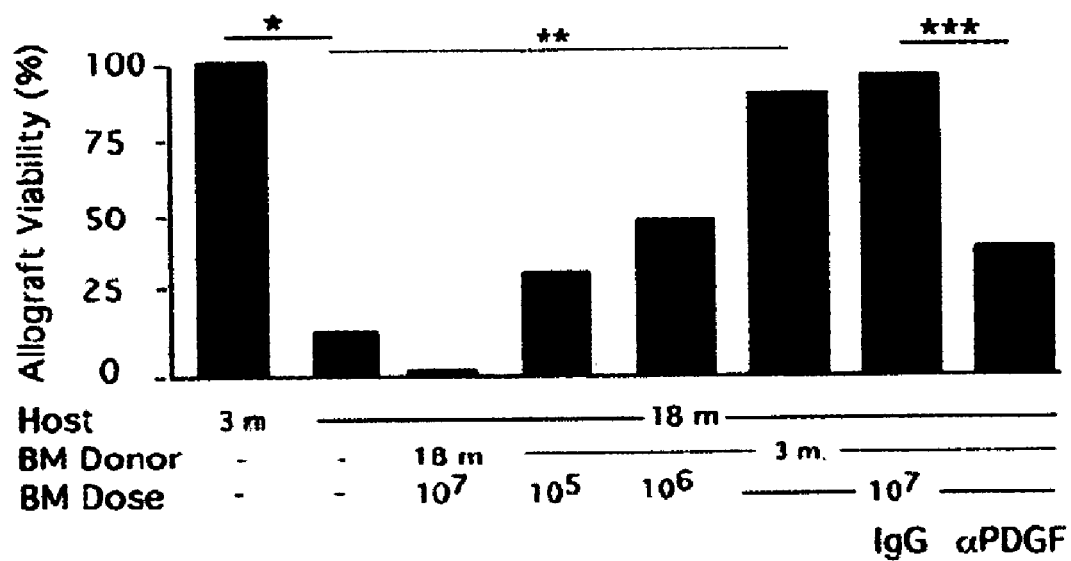

Remarkably, transplantation of bone marrow from 3-month-old mice into intact aging murine hosts maintained the viability and restored the functioning of the exogenous cardiac tissue. See FIG. 3D. However, transplantation of bone marrow from 18-month-old mice failed to reverse the aging-associated decline in cardiac angiogenic function. See FIGS. 3D and 3E. The restoration of the senescent vascular function was a dose dependent response in that the more young bone marrow cells transplanted, the better the viability of the allograft. See FIG. 3E. These data suggest that a subpopulation of the cells that give rise to BM endothelial precursor cells mediates the in vivo reconstitution of the cardiac microvascular communication.

PDGF-AB Protects the Endogenous Heart From Myocardial Infarction

Figure 4A:
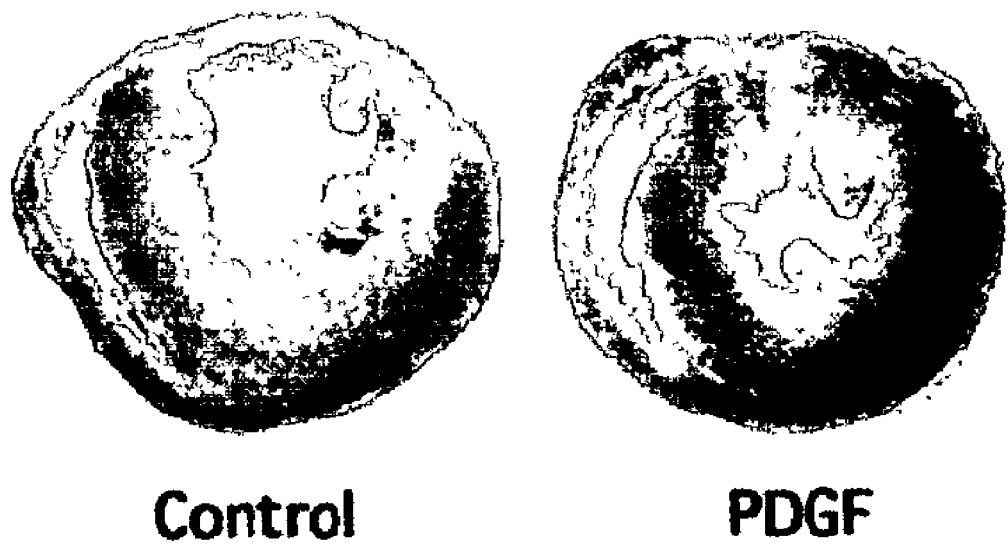
FIG. 4A provides representative photographs of Masson's trichrome stained sections of 4-month-old rat hearts pretreated with PBS or PDGF-AB for 24 h before LAD ligation.
Figure 4B:
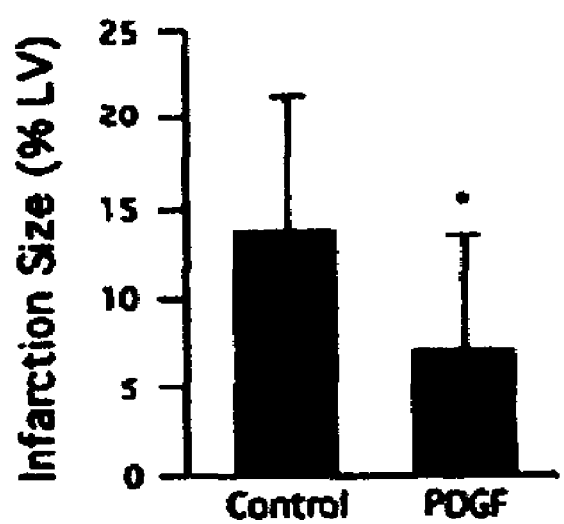
FIG. 4B provides a graph showing the myocardial infarct size scored 14 days after coronary artery ligation (control, n=13; PDGF-AB, n=12). *$P<0.02$, PDGF vs control.
Figure 4C:
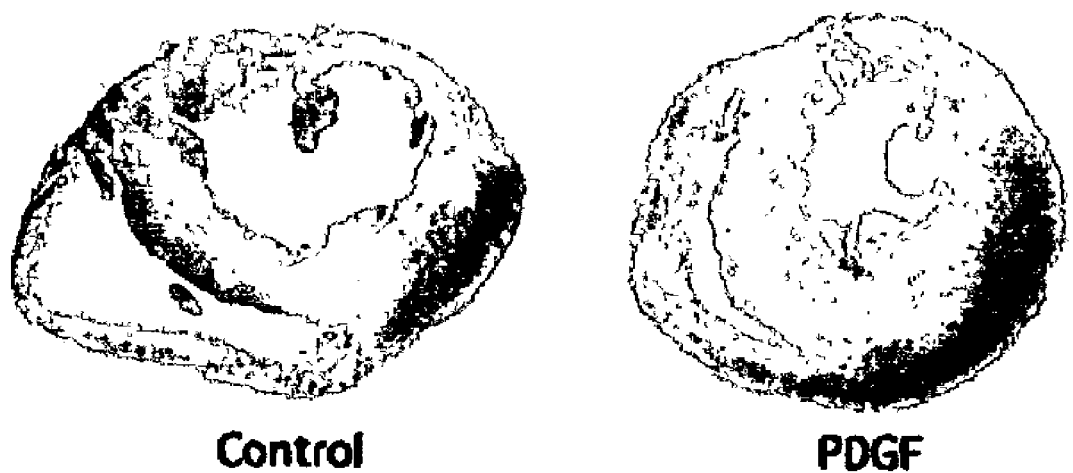
FIG. 4C provides representative photographs of Masson's trichrome staining in 24-month-old rat hearts pretreated with PBS or PDGF-AB 24 h before LAD ligation.
Figure 4D:
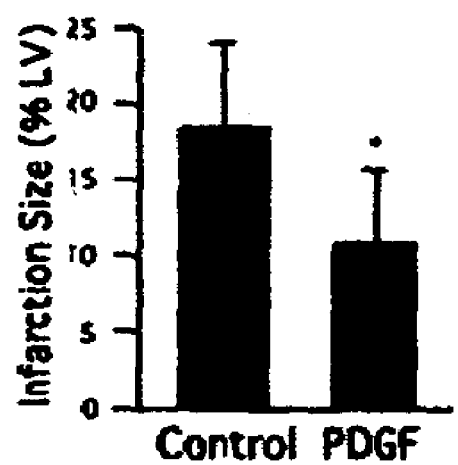
FIG. 4D provides a graph showing myocardial infarct size 14 days after coronary ligation (control, n=5; PDGF-AB, n=7). *$P<0.03$, PDGF vs control.

Experiments were conducted to ascertain whether PDGF-AB pretreatment could significantly reduce the extent of myocardial infarction after LAD ligation. Quantification of myocardial infarction size by Masson's trichrome stain revealed that PDGF-AB reduced the size of myocardial infarction by approximately half in the young adults (FIGS. 4A and 4B). Similarly, the infarction size in 24-month-old heart preinjected with PDGF-AB was approximately half the size of infarctions in control-injected hearts (FIGS. 4C and 4D). Treatment at the time of coronary ligation, however, had no effect on myocardial infarction size (15.7±3.1%; n=3). Hence, a period of pretreatment may be needed.

EXAMPLE 2

PDGF-AB Stimulates Cardiac Myocyte Derivation from Aging Bone Marrow

This Example provides data illustrating that aging bone marrow cells failed to generate cardiac myocytes or to express PDGF-B. However, addition of PDGF-AB restored the cardioplastic potential of aging bone marrow cells and stimulated formation of functional cardiac myocytes that expressed myosin heavy chain and exhibited chronotropic activity in vivo.

Methods

Cell Isolation and Culture

Bone marrow cells were isolated from 3 and 18 month-old wild-type C57B1/6 mice (n=3 each). The mice were sacrificed and the tibias and femurs removed and cut proximally and distally. The bone marrow was flushed with 2% BSA in PBS. The cellular pellets were washed with PBS and plated into 12-well dishes with Iscove's Modified Dulbecco's Medium supplemented with 10% fetal calf serum, 50 μg/mL heparin, 100 μg/mL penicillin, 100 μg/mL streptomycin, 5 ng/mL fibroblast growth factor-2, and 10 ng/mL vascular endothelial growth factor. Additional studies were performed with and without supplemented of PDGF-AB (R&D Systems, 10 ng/mL).

Motion Analysis

Live cells were examined and recorded in real-time under phase microscopy using a Nikon TE 200 inverted microscope equipped with an Orca ER digital camera and imaging software (Simple PCI, Compix). Movies were exported in AVI format. In addition, single frames were obtained to measure systolic and diastolic diameters ($D_s$ and $D_d$, respectively), in order to calculate changes in cell volume ($\Delta V=[(D_d^3-D_s^3)/D_d^3]*100\%$, n=10)

Immunostaining

At the termination of the bone marrow cultures the cells were methanol fixed and stained with monoclonal antibodies for Troponin-T (cardiac isoform) (Clone 13-11, Neomarkers). Immune complexes were visualized using a Vectastain Elite ABC-Nova Red (Vector Laboratories).

Molecular Studies

Total RNA was isolated from individual wells at weekly intervals for 4 weeks (RNeasy, Qiagen) and cDNA was synthesized (Sensicript Reverse Transcriptase, Qiagen). Semi-quantitative PCR was then performed in triplicate using the following primers:

```
β-actin:
(forward)
5'GTGGGCCGCTCTAGGCACCAA3',      (SEQ ID NO:23)
(reverse)
5'CTCTTTGATGTCACGCACGATTTC3';   (SEQ ID NO:24)

PDGF-A:
(forward)
5'TCAAGGTGGCCAAAGTGGAG3',       (SEQ ID NO:25)
(reverse)
5'CTCTCTGTGACAAGGAAGCT3';       (SEQ ID NO:26)

PDGF-B:
(forward)
5'ATCGCCGAGTGCAAGACGCG3',       (SEQ ID NO:27)
(reverse)
5'AAGCACCATTGGCCGTCCGA3';       (SEQ ID NO:28)
```

-continued

```
von Willebrand Factor (vWF):
(forward):
5'TGTCCAAGGTCTGAAGAAGA3',        (SEQ ID NO:29)
(reverse):
5'CAGGACAAACACCACATCCA3';        (SEQ ID NO:30)

PECAM:
(forward):
5'CAAGCGGTCGTGAATGACAC3',        (SEQ ID NO:31)
(reverse):
5'CACTGCCTTGACTGTCTTAAG3';       (SEQ ID NO:32)

αMHC:
(forward):
5'GGAAGAGTGAGCGGCCATCAAGG3',     (SEQ ID NO:33)
(reverse):
5'CTGCTGGAGAGGTTATTCCTCG3'.      (SEQ ID NO:34)
```

Cardiac Myocyte Chronotropic Analysis

In order to assess phenotypic in vivo cardiac chronotropic activity, bone marrow-derived cardiac myocyte aggregates derived from 3 and 18-month-old murine bone marrow cells were transplanted into syngeneic adult hosts as previously described (n=5 each). Edelberg et al. (2002) *J Appl Physiol.* 92:581-5. Briefly, sets of mice were anesthetized with Avertin IP and prepared for aggregate engraftment by subcutaneous pinnal injections of PDGF-AB (20 ng/20 μL PBS). The following day, myocyte aggregates were physically dissociated and suspended in PBS ($5 \times 10^4$ cells/20 μL). These suspensions were transferred into a subdermal pinnal pocket, which was then sealed via gentle pressure with forceps. Electrocardiographic (ECG) activity of the endogenous heart and transplanted aggregates to assess chronotropic activity was performed 5-7 days post-transplantation following anesthetization with Avertin IP. ECG data was acquired as previously described. Christini et al. *Amer J Physiol.* 2001; 280:H2006-2010. Following baseline recordings, chronotropic adenergic responsiveness was measured through local administration of isoproterenol (100 ng/10 μL PBS). Statistical significance was determined by student's t-test.

Results

Cardioplastic Potential of Young Bone Marrow Cells

Figure 5:
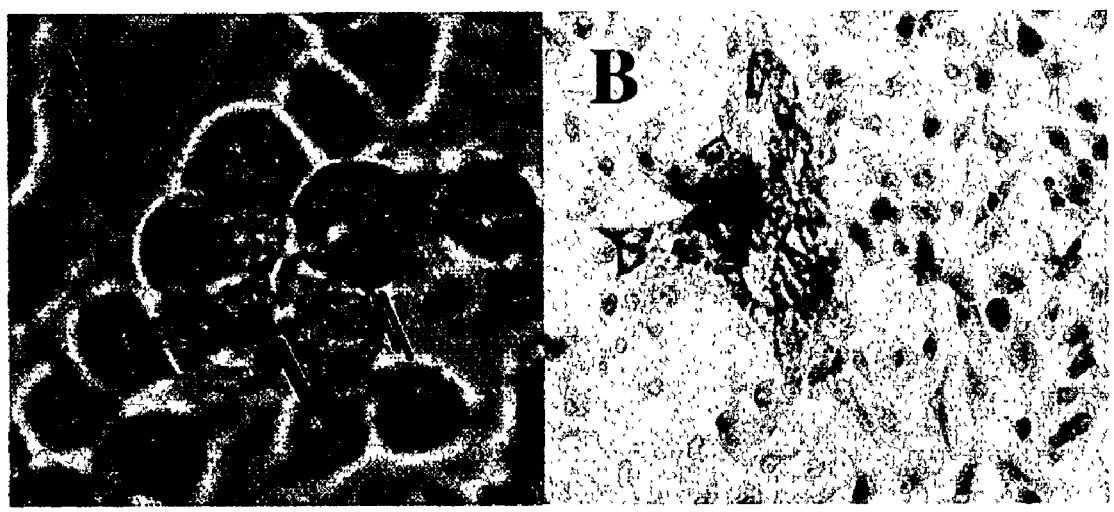
FIG. 5A provides a photomicrograph of a representative 3-month-old bone marrow-derived cardiac myocyte aggregate that exhibited spontaneous chronotropy after 4 weeks of tissue culture: parallel bars represent single cell diastole (outside bars) and systole (inside bars) (15±4% cell volume change) (bar=10 μm) (movie on disc).
FIG. 5B provides a photomicrograph of representative 3-month-old bone marrow-derived cell cultures immunostained for troponin T (bar=25 μm).

Bone marrow cells harvested from 3-month old mice grown under conditions supporting endothelial cells developed spontaneous chronotropic activity indicative of cardiac myocyte cultures (FIG. 5A). Bone marrow cells harvested from 18-month old mice grown under similar conditions did not exhibit such chronotropic activity. The cardioplastic potential of the young bone marrow cultures was further evidenced by immunostaining for troponin T (FIG. 5B), however, older bone marrow cultures did not stain positively for troponin T. These results indicate that the molecular pathways regulating the differentiation of cardiac myocytes from the aging bone marrow are impaired.

In order to develop strategies to restore the generation of cardiac myocytes from aging bone marrow cells, older bone marrow cells were exposed to factors involved in the cardiac myocyte-endothelial communication pathway. Molecular analysis revealed that PDGF isoforms were induced at the same time as cardiac myocyte-specific αmyosin heavy chain (αMHC), however, vWF was expressed after PDGF and αMHC (FIG. 6A). vWF is a marker for cardiac myocyte-endothelial PDGF communication. Edelberg et al. *J Clin Invest.* 1998;102:837-43. Addition of PDGF-AB increased the kinetics of cardiac myocyte generation as evidenced by αMHC expression in half the time of the bone marrow cells cultured in the absence of unsupplemented media (FIG. 6B).

The in vivo viability of the bone marrow-derived cardiac myocytes was confirmed by transplantation of the cells into pinna of syngeneic mice. After transplantation, electropotential signals were observed from the bone marrow-derived cardiac myocyte aggregates. Greater than 80% increase in chronotropic activity was observed (226+/−60 vs. 120+/−18 depolarizations/min, baseline, p<0.05) (FIG. 7C).

Restoring Cardioplastic Potential of Aging Bone Marrow Cells

Figure 6:
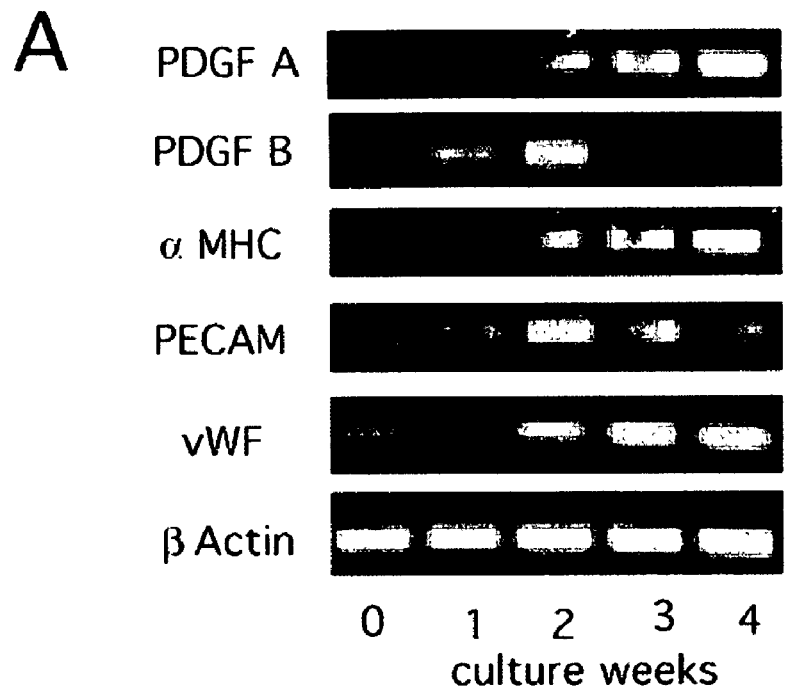
FIG. 6A provides a representative gel of RT-PCR products illustrating temporal gene expression of 3-month-old bone marrow-derived cells.
FIG. 6B provides a representative gel of RT-PCR products illustrating temporal gene expression of 3-month-old bone marrow-derived cells in the presence and absence of exogenous PDGF.
FIG. 6C provides a representative graph of in vivo chronotropic activity as a function of time in a 3-month-old bone marrow-derived cardiac myocyte before and after adrenergic stimulation.
Figure 6:
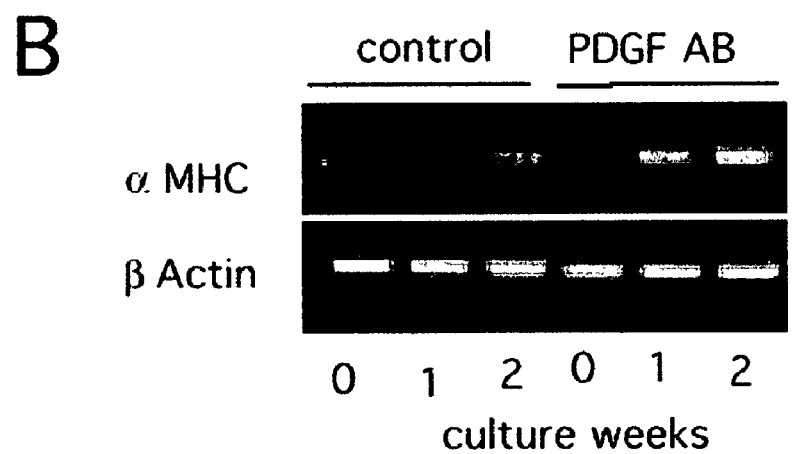
Figure 6:
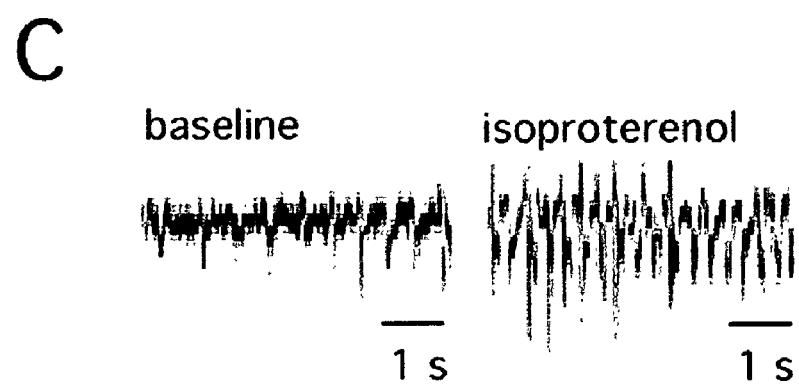
Figure 7:
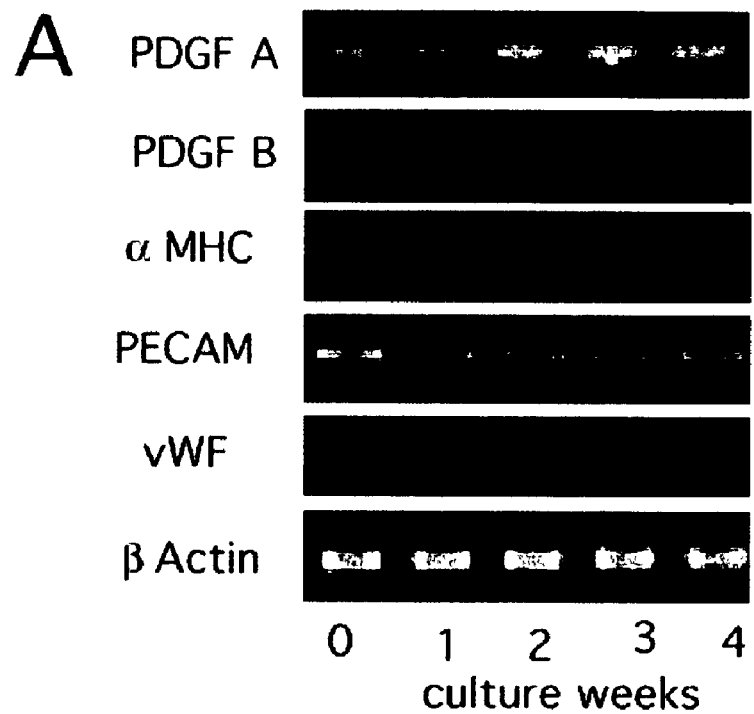
FIG. 7A provides a representative gel of RT-PCR products illustrating temporal gene expression profiles of 18-month-old bone marrow-derived cells.
FIG. 7B provides a representative gel of RT-PCR products illustrating αMHC expression in 18-month-old bone marrow-derived cells in the presence and absence (control) of exogenous PDGF. As a further control, β-actin expression was also observed FIG. 7C provides a representative graph of in vivo chronotropic activity as a function of time in a PDGF-induced 18-month-old bone marrow-derived cardiac myocyte before and after adrenergic stimulation.
Figure 7:
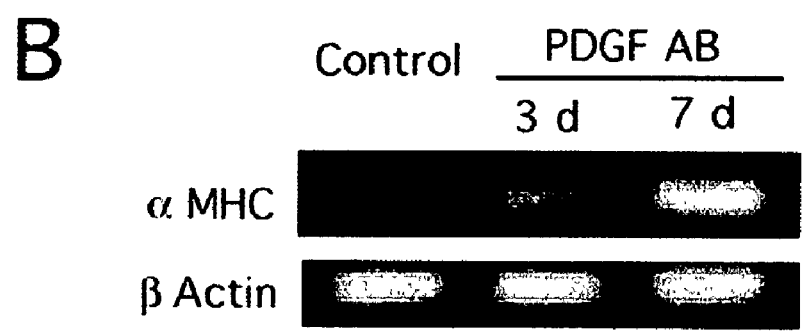
Figure 7:
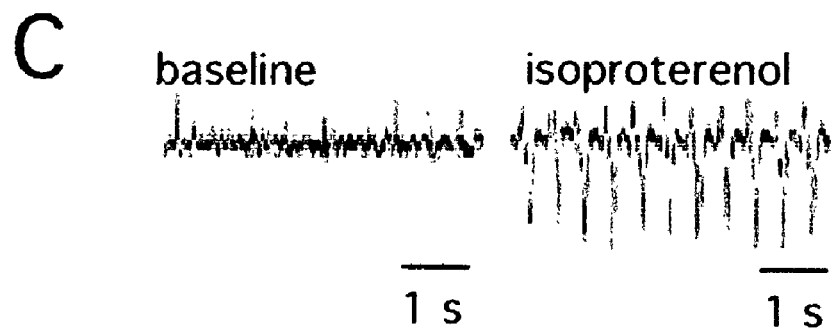

Unlike young bone marrow, cells derived from the aging bone marrow did not express PDGF-B, αMHC, or vWF (compare FIG. 6A and FIG. 7A). However, as shown FIG. 7B, 18-month-old bone marrow cultured in the presence of exogenous PDGF-AB did express αMHC. Moreover, the resultant cardiac myocyte aggregates derived from these cultures demonstrated phenotypic electrocardiographic activity in vivo (see FIGS. 6C and 7C). Greater than a 60% fold increase in chronotropic activity was observed in 18-month-old bone marrow cultured in the presence of exogenous PDGF-AB (137+/−10 depolarizations/min, baseline,) compared to 18-month-old bone marrow cultured in the absence of exogenous PDGF-AB (83+/−24 depolarizations/min, baseline, p<0.05)(FIG. 7C).

These results indicate: (1) PDGF mediates the generation of cardiac myocytes from young bone marrow, (2) when PDGF-B induction does not occur in aging bone marrow cells, cardiac myocyte generation is impaired, and (3) addition of exogenous PDGF can stimulate and/or restore myocyte generation from bone marrow cells.

REFERENCES

1. Makino S, Fukuda K, Miyoshi S, et al. Cardiomyocytes can be generated from marrow stromal cells in vitro. *J Clin Invest.* 1999; 103:697-705.
2. Malouf N N, Coleman W B, Grisham J W, et al. Adult-derived stem cells from the liver become myocytes in the heart in vivo. *Am J Pathol.* 2001;158:1929-35.
3. Orlic D, Kajstura J, Chimenti S, et al. Bone marrow cells regenerate infarcted myocardium. *Nature.* 2001;410:701-5.
4. Jackson K A, Majka S M, Wang H, et al. Regeneration of ischemic cardiac muscle and vascular endothelium by adult stem cells. *J Clin Invest.* 2001;107:1395-402.
5. Hakuno D, Fukuda K, Makino S, et al. Bone Marrow-Derived Regenerated Cardiomyocytes (CMG Cells) Express Functional Adrenergic and Muscarinic Receptors. *Circulation.* 2002;105:380-386.
6. Rafii S, Shapiro F, Pettengell R, et al. Human bone marrow microvascular endothelial cells support long-term proliferation and differentiation of myeloid and megakaryocytic progenitors. *Blood.* 1995;86:3353-63.
7. Davis T A, Lee K P. Ex vivo expansion of primitive murine hematopoietic progenitor cells on porcine endothelial cells. *Transplant Proc.* 1997;29:2005.
8. Mohle R, Salemi P, Moore M A, Rafii S. Expression of interleukin-5 by human bone marrow microvascular endothelial cells: implications for the regulation of eosinophilopoiesis in vivo. *Br J Haematol.* 1997;99:732-8.
9. Rafii S, Mohle R, Shapiro F, et al. Regulation of hematopoiesis by microvascular endothelium. *Leuk Lymphoma.* 1997;27:375-86.
10. Yourey P A, Gohari S, Su J L, Alderson R F. Vascular endothelial cell growth factors promote the in vitro development of rat photoreceptor cells. *J Neurosci.* 2000;20: 6781-8.

11. Palmer T D, Willhoite A R, Gage F H. Vascular niche for adult hippocampal neurogenesis. *J Comp Neurol.* 2000; 425:479-94.
12. Wang T, FitzGerald T J, Haregewoin A. Differential expression of nitric oxide synthases in EGF-responsive mouse neural precursor cells. *Cell Tissue Res.* 1999;296: 489-97.
13. Edelberg J M, Tang L, Hattori K, et al. Young Adult Bone Marrow-Derived Endothelial Precursor Cells Restore Aging-Impaired Cardiac Angiogenic Function. *Circ. Res.* 2002;90:e89-e93.
14. Edelberg J M, Aird W C, Wu W, et al. PDGF mediates cardiac microvascular communication. *J Clin Invest.* 1998; 102:837-43.
15. Edelberg J M, Lee S H, Kaur M, et al. Platelet-Derived Growth Factor-AB Limits the Extent of Myocardial Infarction in a Rat Model: Feasibility of Restoring Impaired Angiogenic Capacity in the Aging Heart. *Circulation.* 2002;105:608-613.
16. Weinsaft J W, Edelberg J M. Aging-Associated Changes in Vascular Activity—A Potential Link to Geriatric Cardiovascular Disease. *Amer J Geriatric Cardiology.* 2001; 10:348-354.
17. Edelberg J M, Jacobson J T, Gidseg D S, et al. Enhanced myocyte-based biosensing of the blood-borne signals regulating chronotropy. *J Appl Physiol.* 2002;92:581-5.
18. Christini D J, Walden J, Edelberg J M. Direct biologically-based biosensing of dynamic physiological Function. *Amer J Physiol.* 2001;280:H2006-2010.
19. Betsholtz C. Role of platelet-derived growth factors in mouse development. *Int J Dev Biol.* 1995;39:817-25.
20. Ataliotis P, Mercola M. Distribution and functions of platelet-derived growth factors and their receptors during embryogenesis. *Int Rev Cytol.* 1997;172:95-127.

What is claimed:

1. A culture comprising isolated bone marrow cells, PDGF AB, VEGF, heparin FGF and cardiac myocytes derived therefrom, wherein the concentrations of PDGF, VEGF and FGF in the culture are sufficient to generate myocytes from the bone marrow cells.

2. The culture of claim 1, wherein the cells are human cells.

3. The culture of claim 1, wherein the bone marrow cells are from an autologous donor.

4. The culture of claim 1, wherein the bone marrow cells are senescent bone marrow cells.

5. The culture of claim 1, wherein the culture contains at least 10 ng/ml PDGF AB, at least 10 ng/ml VEGF and at least 5 ng/ml FGF.

6. The culture of claim 1 further comprising fetal calf serum.

* * * * *

UNITED STATES PATENT AND TRADEMARK OFFICE
CERTIFICATE OF CORRECTION

PATENT NO. : 7,514,261 B2
APPLICATION NO. : 10/215271
DATED : April 7, 2009
INVENTOR(S) : Edelberg et al.

It is certified that error appears in the above-identified patent and that said Letters Patent is hereby corrected as shown below:

On the Title Pg, Item (56), under "Other Publications", line 11,
delete "Transplatation" and insert -- Transplantation --, therefor.

On the Title Pg, Item (56), under "Other Publications", line 20,
delete "Endothelilial" and insert -- Endothelial --, therefor.

On the Title Pg, Item (56), under "Other Publications", line 43, delete "bome" and insert -- bone --, therefor.

On the Title Pg, Item (56), under "Other Publications", line 45,
delete "eosinophilopoieses" and insert -- eosinophilopoiesis --, therefor.

In column 43, line 32, in Claim 1, delete "heparin FGF" and insert -- heparin, FGF --, therefor.

Signed and Sealed this

Twenty-second Day of December, 2009

David J. Kappos
*Director of the United States Patent and Trademark Office*